(12) United States Patent
Neev

(10) Patent No.: US 8,313,480 B2
(45) Date of Patent: Nov. 20, 2012

(54) DEVICE AND METHOD FOR TREATING SKIN DISORDERS WITH THERMAL ENERGY

(76) Inventor: Joseph Neev, Lake Forest, CA (US)

( * ) Notice: Subject to any disclaimer, the term of this patent is extended or adjusted under 35 U.S.C. 154(b) by 1771 days.

(21) Appl. No.: 11/234,771

(22) Filed: Sep. 23, 2005

(65) Prior Publication Data

US 2006/0074468 A1   Apr. 6, 2006

Related U.S. Application Data

(60) Provisional application No. 60/615,510, filed on Oct. 2, 2004, provisional application No. 60/678,968, filed on May 9, 2005, provisional application No. 60/704,602, filed on Aug. 1, 2005.

(51) Int. Cl.
*A61B 18/18* (2006.01)
(52) U.S. Cl. .................. 606/9; 606/27; 606/28; 607/88; 607/96
(58) Field of Classification Search .................. None
See application file for complete search history.

(56) References Cited

U.S. PATENT DOCUMENTS

| | | | |
|---|---|---|---|
| 4,292,971 A | | 10/1981 | Smit et al. |
| 4,410,132 A | * | 10/1983 | Levine ............... 236/11 |
| 5,154,707 A | * | 10/1992 | Rink et al. ........... 606/12 |
| 5,207,671 A | | 5/1993 | Franken |
| 5,571,216 A | | 11/1996 | Anderson |
| 5,620,478 A | | 4/1997 | Eckhouse |
| 5,720,894 A | | 2/1998 | Neev |
| 5,817,641 A | | 10/1998 | Waldman et al. |
| 5,830,208 A | * | 11/1998 | Muller ............... 606/9 |
| 5,868,732 A | | 2/1999 | Waldman et al. |
| 5,879,346 A | | 3/1999 | Waldman et al. |
| 5,885,211 A | | 3/1999 | Eppstein et al. |
| 5,906,609 A | | 5/1999 | Assa et al. |
| 5,989,283 A | | 11/1999 | Wilkens |
| 6,050,990 A | | 4/2000 | Tankovich et al. |
| 6,134,475 A | | 10/2000 | Will |
| 6,156,030 A | | 12/2000 | Neev |
| 6,168,590 B1 | | 1/2001 | Neev |
| 6,228,082 B1 | | 5/2001 | Baker et al. |
| 6,280,438 B1 | * | 8/2001 | Eckhouse et al. ........ 606/9 |
| 6,402,739 B1 | | 6/2002 | Neev |
| 6,408,212 B1 | | 6/2002 | Neev |
| 6,482,199 B1 | | 11/2002 | Neev |
| 6,508,785 B1 | | 1/2003 | Eppstein |
| 6,685,699 B1 | | 2/2004 | Eppstein et al. |
| 6,717,102 B2 | | 4/2004 | Neev |
| 6,922,578 B2 | | 7/2005 | Eppstein et al. |
| 7,163,536 B2 | * | 1/2007 | Godara ............... 606/34 |
| 7,494,492 B2 | | 2/2009 | Da Silva |
| 2002/0169442 A1 | * | 11/2002 | Neev ............... 606/9 |

(Continued)

FOREIGN PATENT DOCUMENTS

WO   WO 02089688 A1 * 11/2002

*Primary Examiner* — Gregory A Morse
*Assistant Examiner* — Lynsey Crandall
(74) *Attorney, Agent, or Firm* — Richard B. Cates

(57) ABSTRACT

A device and a method for thermal treatments of target material with various thermal interactions are disclosed. A preferred treatment includes Thermal Heat Shuttle that transports a predetermined known quota of energy to the target surface. In particular, the launching of thermal energy quanta from various energy sources in lumps of energy quanta and leading to the treatment and healing of a variety of skin conditions are disclosed.

11 Claims, 30 Drawing Sheets

U.S. PATENT DOCUMENTS

| | | | |
|---|---|---|---|
| 2003/0018373 A1* | 1/2003 | Eckhardt et al. | 607/94 |
| 2004/0005349 A1* | 1/2004 | Neev | 424/443 |
| 2006/0129214 A1 | 6/2006 | DaSilva et al. | |
| 2006/0142750 A1 | 6/2006 | DaSilva et al. | |

* cited by examiner

DEVICE AND METHOD FOR TREATING SKIN DISORDERS WITH THERMAL ENERGY

CROSS REFERENCE TO RELATED APPLICATIONS

This application claims priority benefit of provisional application Nos. 60/615,510 filed on Oct. 2, 2004, 60/678,968 filed on May 9, 2005, and 60/704,602 filed on Aug. 1, 2005. The contents of these provisional applications are hereby incorporated by reference in their entirety.

BACKGROUND OF THE INVENTION

Skin disorders, such as acne, can be irritating and embarrassing. The major disease of skin associated with sebaceous follicles is acne vulgaris. This is also the most common reason for visiting a dermatologist in the United States. There are many treatments, but no cures for acne. These include antibiotics (which inhibit growth of p. acnes bacteria which play a role in acne), retinoids such as Accutane® (isotetinoin, which reduces sebaceous gland output of sebum), and antimicrobials such as benzoyl peroxide.

Acne lesions result from the rupture of a sebaceous follicle, followed by inflammation and pus (a "whitehead"), or by accumulation of plugged material in the sebaceous follicle (a "blackhead"). This condition has two major requirements: (1) plugging of the upper portion of the follicle, and (2) an increase in sebum production. The upper portion of the follicle, i.e., the "pore" into which sebum is secreted and which is directly in contact with the skin surface, is called the infundibulum. A plug forms in the infundibulum from cells, sebum, bacteria, and other debris. The sebaceous gland continues to produce sebum (an oily fluid), stretching the infundibulum until either it or some lower portion of the follicles ruptures.

In most males, acne is worst in the teenage years and then subsides, in women, teenage acne is often followed by menstrual acne flares well into adulthood. It is well known in the art that both plugging of the infundibulum and high sebaceous gland activity are necessary for an acne lesion to develop. Several methods known in the art are aimed at reducing gland activity or inhibiting bacteria. The drug Acutane is approved by the FDA but is taken orally and has severe side effects such as skin dryness, birth defects and sever depression. Light based method in conjunction with cooling are used to at least partially disable the sebaceous glands. These methods too result in skin dryness due to the damage cause to the sebaceous glands and usually require high energy level which are potentially hazardous and require doctor-only operation. As the consequence of the relative invasiveness of the procedure, interaction with live tissue, and high laser power level needed, the instrument are relatively expensive. Both methods require time to take effect and results are generally monitored over period of weeks and months.

SUMMARY OF THE INVENTION

It is therefore useful to have a method and a device that is relatively low cost and effective in treating active acne condition. Such a method and a device is contemplated by the present invention. It includes a low power light or electromagnetic energy source or a source of electric power. The energy source is used to rapidly generate thermal energy deposition in the upper layers of the skin which then result in opening and dainagle of the pores. The enlarging of the pores then results in drainage of the sebum and any other liquid or debris trapped within the pores, and with them, the acne causing bacteria or any other infectious or diseases causing components.

In particular, such devices can be hand held and constructed of low power photographic light bulb such as the ones used in single-use or small digital cameras. Other energy sources can be heating elements including electrical resistors that can generate high temperatures by use of a current or an electric heater.

Such energy source can be powered by low cost transformers or batteries or electric line, be controlled by small electronic board and discharge their energy from a storage capacitor at variable discharge pulse durations. Such an assembly can be very inexpensive and as result yield low cost home or consumer use device or low cost, cosmeticians, aestheticians or physician use devices.

Because energy is delivered to the uppermost layers of the skin only to allow opening of the pores, the method and the devices are very safe. (energy diffusing below the epidermal dermal junction) are not high enough to cause collateral damage.)

Because the expansion is very rapid and the drainage of the pore begins immediately, the response of the acne is very rapid and results can be observed from as little as a few hours or less.

The method utilizes the principle of application of thermal energy to the upper section of the skin such that the skin upper layers are forced to expand (fully or partially) in a manner that results in temporary expansion of the pores and pore openings, thereby treating skin disorder. The method and devices envision thermal energy delivered directly from a source, via the mediation of a heating element capable of depositing such expansion-causing thermal energy on the surface of the skin. One embodiment envisions light or electromagnetic (EM) energy as the energy source for the expansion causing energy. In particular one such preferred embodiment envisions the use of low cost flash lamp of the kind used in disposable or digital (or single-use) cameras, to deposit such thermal energy in the skin. This embodiment further envisions the possibility of use of an absorbing intermediate substance which can partially or fully absorb the EM energy to create thermal energy deposition on the surface of the skin.

The use of such low power light source significantly reduces the cost of the systems, their size, and thus make such treatment devices useful for home and consumer use. The use of a system which to a large extent use components of disposable, single use, or consumer digital camera, also increases safety level in a significant way (people expose themselves and others multipmillion times a day to such energy level while taking photographs), and thus reduces both the risk of collateral damage and unwanted damage and risk to tissue and human.

Electrical energy to heat tissue and treat skin conditions can also be used. Here however, there is a risk of over-heating, as in all case of application of energy to tissue, but in addition, there is a risk of electric shock and electrocution. To mitigate these risks the invention also contemplates the use of a transport of heat from an electrical heat source to the target tissue as well as other components to limit the amount of electric energy and heat deposited in the tissue.

The invention further contemplates a heat shuttle that is "loaded up with thermal energy" and then delivers its thermal energy to the skin in lump quanta of thermal energy. The invention further envisions the use of an electro-optic system such as a laser, or a flash lamp with a topically applied high absorbing substance or a film capable of absorption of such optical energy.

More specifically, the method and apparatus described herein are also applicable for treating skin conditions and skin ailments and in particular, acne conditions. Acne lesions result from the rupture of a sebaceous follicle, followed by inflammation and pus (a "whitehead"), or by accumulation of plugged material in the sebaceous follicle (a "blackhead"). The creation of this condition requires two elements: (1) plugging of the upper portion of the follicle, and (2) an increase in sebum production. The upper portion of the follicle, i.e., the "pore" into which sebum is secreted and which is directly in contact with the skin surface, is called the infundibulum. A plug forms in the infundibulum from cells, sebum, bacteria, and other debris. The sebaceous gland continues to produce sebum (an oily fluid), stretching the infundibulum until either it or some lower portion of the follicles ruptures. The method and apparatus described herein, allows the skin upper layers to temporary expand under the influence of energy deposited into this target region thus allowing treatment of the skin disordered, and in particular, acne.

The invention contemplates the use of several energy sources to achieve the acne and skin treatment effects including: optical energy, optothermal conversion of optical energy to thermal—tissue expanding energy, electrical energy and electro-thermal conversion of electrical energy to thermal energy and mechanical energy source. The invention also contemplates, an electrical energy source that heats up an intermediate material that is then brought into contact with the tissue surface to achieve treatment and expansion. The invention also contemplate such electrical heated intermediate material being disconnected from the heat source and then brought into contact into with the targeted tissue. Alternatively the heater source may remain connected to the electrical source and the electrical source discharge and deliver its energy to the tissue after said energy is converted to thermal energy in the device.

BRIEF DESCRIPTION OF THE DRAWINGS

FIG. 11b illustrates another exemplary circuit driving an optical discharge hand held acne treatment device.

DESCRIPTION OF PREFERRED EMBODIMENTS

The object of this invention is to provide a device and a method for treating skin illnesses and improving skin condition and appearance. Making use of thermal energy the invention contemplates treating skin conditions such as wrinkles, finelines, skin lesions, cysts, warts, and improving the appearance of the skin. Yet another object of the present invention is to provide a low cost, safe hand held device for treating the outer layer of the tissue and skin without undesirable injuries to the skin.

In particular the invention aims at treating skin conditions and enhancing the appearance of the skin by depositing sufficient amount of energy into the skin surface to mitigate skin ailments and also allows external products to be able to better penetrate the skin surface thus enhancing skin conditions and healing the skin. Further, the invention aims at doing the above by minimizing collateral damage to the skin.

The invention also contemplates accomplishing many of the above tasks by using a low cost hand held devices. Such a device is designed to utilize inexpensive components and is often powered by batteries or transformers. It limits the amount of energy deposited to the surface of the skin, resulting in relatively large concentration of energy at the upper surface of the skin so that beneficial physical effects are created healing the skin and improving its condition, but the amount of energy that the device deposit into the skin is not large enough to create collateral or unwanted damage to the living tissue of the skin.

In one preferred embodiment, the invention envisions constructing a device utilizing the low cost components of disposable, single use, or digital cameras to generate light energy, converting it to heat, and thus healing the skin and improving skin conditions.

Figure 1:
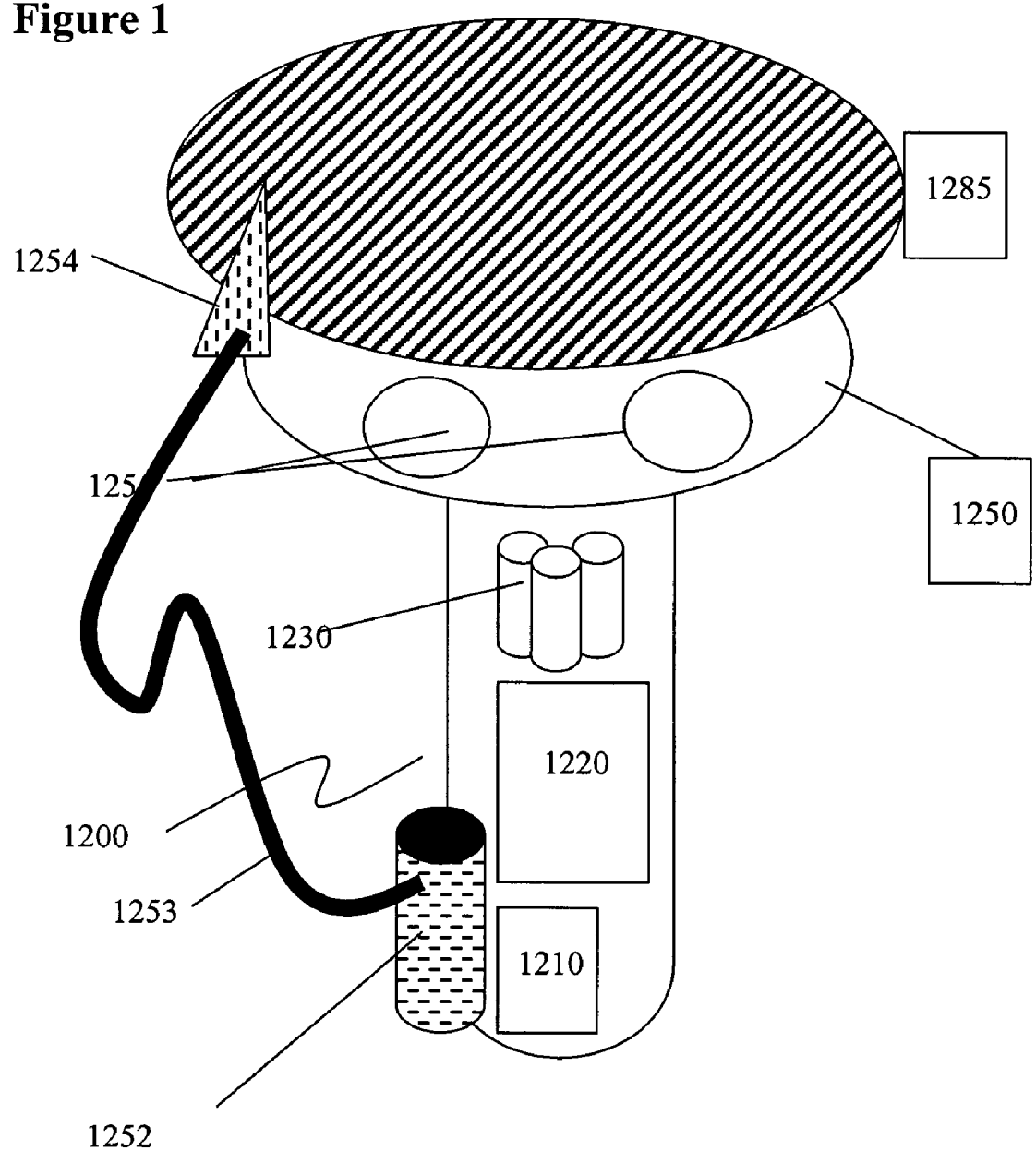
FIG. 1 shows a sectional view taken through the handheld acne treatment device that uses a light energy sources and high absorbing intermediate layer to deliver energy into the skin.

In an embodiment shown in FIG. 1, the invention contemplates a device comprising a casing 1200 that contains a power source 1210 (a battery or a wall-plug transformer, or a power supply or a power cord), a controlling circuit 1220, plurality of electric energy storage capacitors 1230, wires and connections to the treatment head 1250 where a plurality of treatment windows 1255 may be incorporated. The Figure also shows a layer of absorbing substance 1285 contemplated for use in the present invention for conversion of the treatment source energy into thermal energy.

Figure 2:
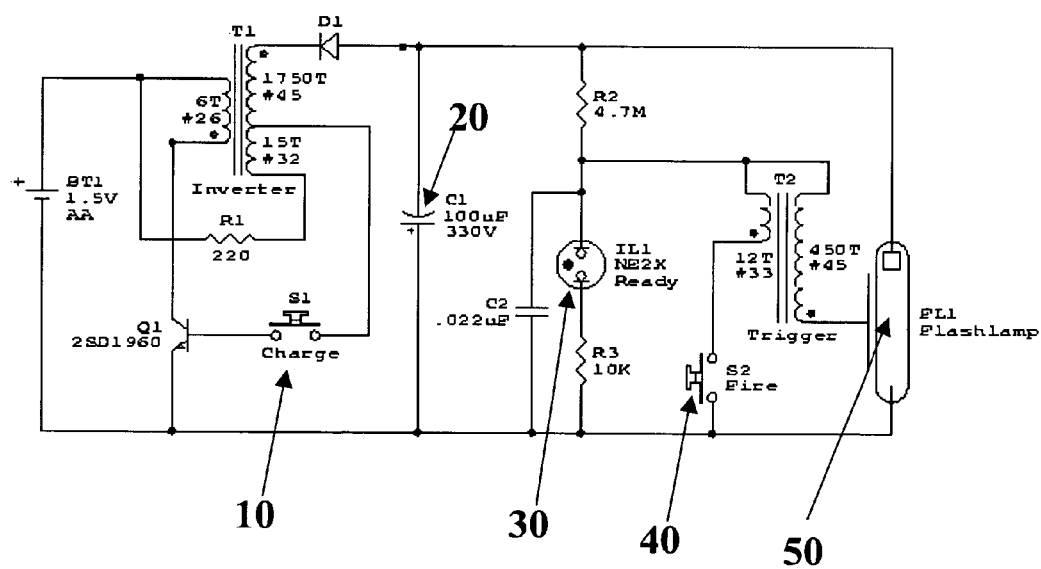
FIG. 2 shows an exemplary circuit diagram for pulsing the energy source (light, electrical, or mechanical discharge, or preferably, a flash lamp)

In such a preferred embodiment the device is aimed at treating acne. In this preferred embodiment the device utilizes a small flash lamp such as the Perkin Elmer CGD 0013 or Perkin Elmer CGAC 2018 or Perkin Elmer BGAC 3022. Such flash lamps can be powered and controlled by an electronic board of the type shown in FIG. 2. Here, a switch 10 is turned on to activate the device and charge a capacitor 20. When the capacitor is fully charged a lamp 30 (or LED) turns on and the circuit is ready to fire. Push button 40 is pressed to trigger the discharge of the capacitor 20 which fires the flash lamp 50. After firing, the capacitor 20 again begins to charge and after several seconds (depending on battery and resistance) is fully charged. This circuit releases a maximum energy per pulse of $\frac{1}{2} CV^2$ where C is the capacitor capacitance and V is the final voltage across the capacitor.

Figure 3:
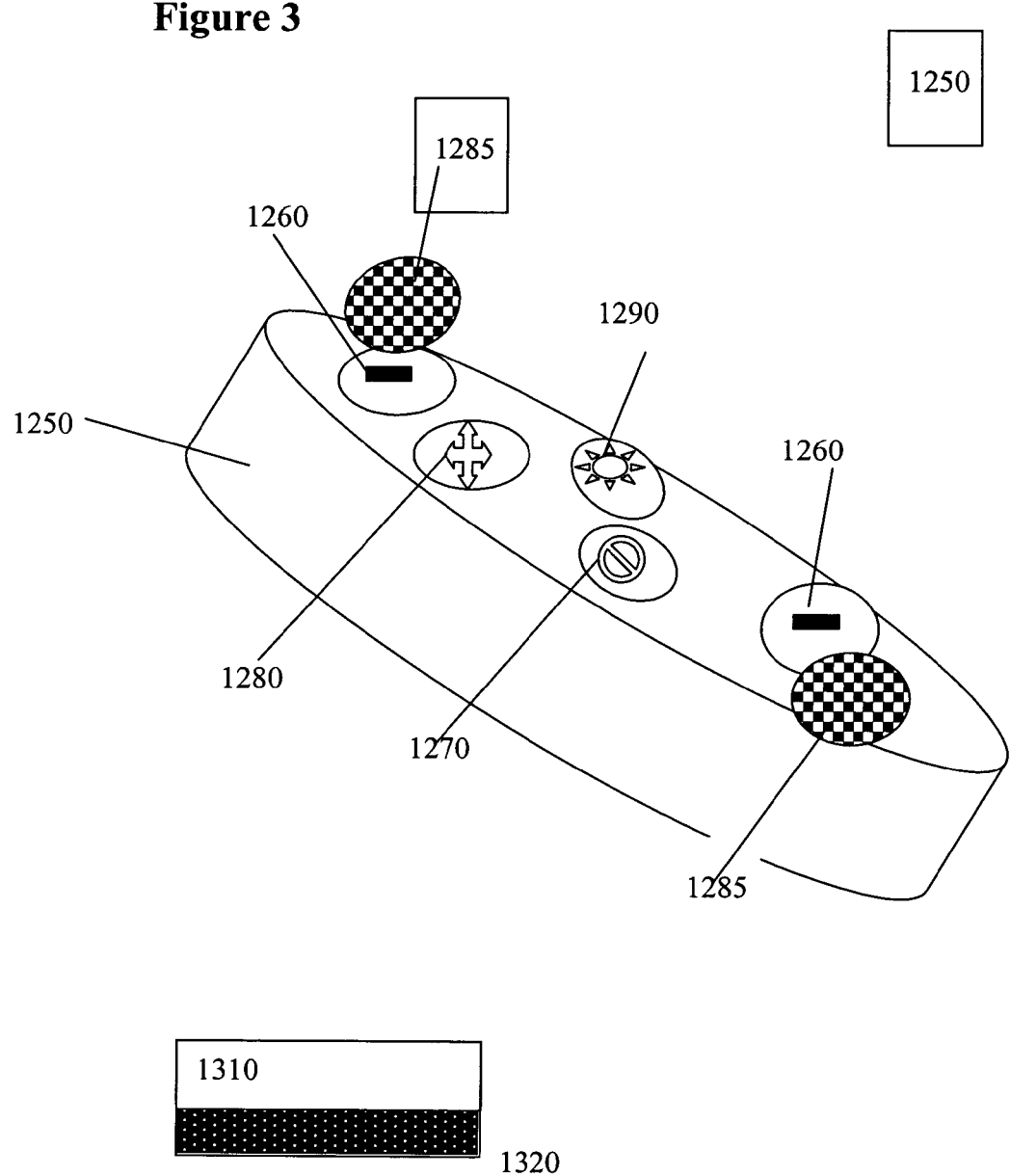
FIG. 3 shows a sectional view taken through the Treatment Head of a hand-held acne and skin treatment device, including light energy windows with optional light absorbing intermediate substance, electrical heater treatment window, and other forms of energy sources.

FIG. 3 shows a treatment head 1250 which contains a combination of the following elements: a plurality of flash lamps 1260, a plurality of electrical heating elements 1270, a plurality of mechanical scraping or buffing elements 1280, a plurality of suction devices 1290. The treatment head 1250 may contain some of the above elements. For example, it may contain only a plurality of flash lamps 1260. Or it may contain a plurality of electric treatment windows, or it may contain a combination of both plurality of flash lamps and electric heating treatment windows. FIG. 3 also shows a plurality of partially or fully absorbing layers 1285 over the light generating elements 1260 or flash lamps 1260 and between the light generating elements and the targeted skin area. In a preferred embodiment the absorbing layer can be placed in front of the lamp or removed from its intermediate position between the lamp window and the surface of the skin. Furthermore, the absorption layer can be made of the following components (see FIG. 3):

A backup layer 1310 that provides some rigidity, and a front layer of absorbing material 1320. The backup layer can be a transparent layer and can be made, for example, from glass or high temperature plastic, capable of sustaining the temperature generated by the device at the absorbing layer and without deforming or substantially deteriorated.

Alternatively, the absorbing material can be embedded or deposited or painted on the surface of the backup transparent layer 1310 on the surface placed against the skin. In an alternative embodiment, the absorbing material can be made of carbon particle coated over a substrate layer 1310. Or the absorbing particles, for example carbon particles, can be embedded in a transparent layer, for example a layer of glass or plastic. Alternatively the glass or plastic can be etched or scratched with grooves that retain the absorbing material at its surface. The absorbing material should be deposited close to or on the surface of the substrate layer 1310 that is closer to the target skin surface. Another embodiment utilizes a thin heat conducting layer, for example a layer of metal such as gold or copper or other heat conducting materials, as the substrate 1310, with an absorbing layer 1320 placed on the side which is farther away from the target skin surface and closer to the light energy source. In this embodiment, the absorbing layer 1320 can be etched, painted, embedded or coated onto the metal substrate layer 1310. Alternatively the substrate layer 1310 can be machined or conditioned (e.g. with electron beam or laser beam, excimer laser beam, chemical etch, or any other method allowing the surface of a metal to trap light energy or enhanced the surface of the metal to absorb the light energy). The light energy would be rapidly conducted towards the skin surface in contact with the metal layer 1310 on the opposite surface of the high absorbing layers.

Figure 4:
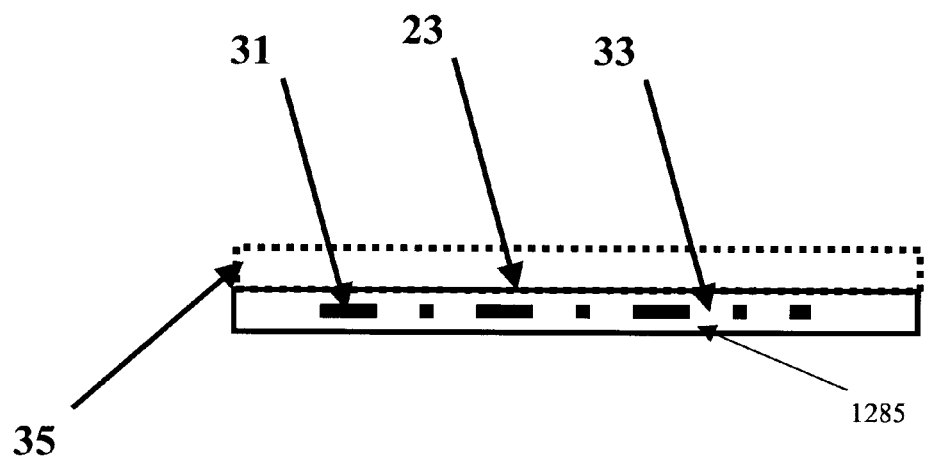
FIG. 4 shows a sectional view taken through another embodiment of the treatment head and high absorbing intermediate substance composition.
Figure 4:
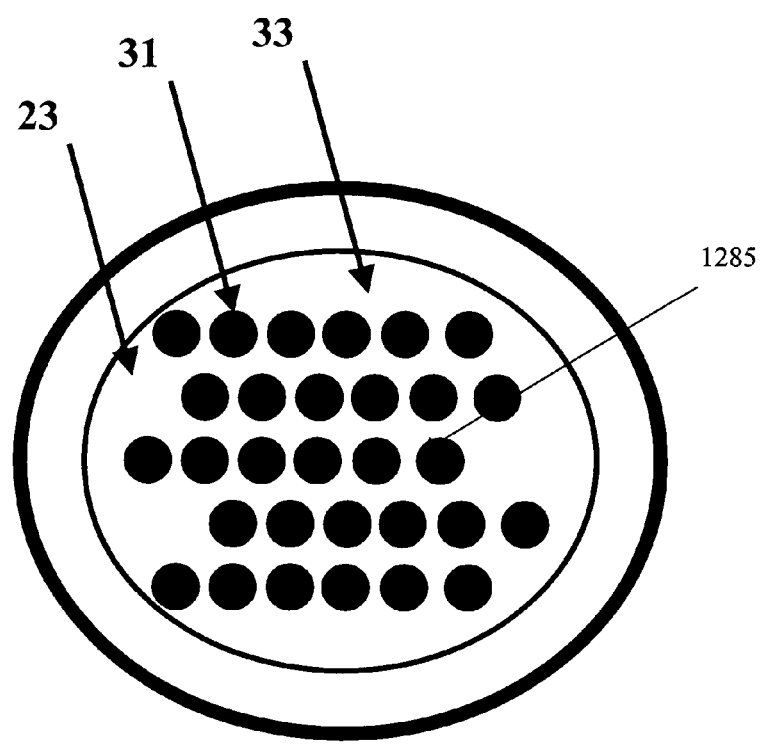

FIG. 4 shows a front and a side view of another preferred embodiment of the absorbing layer of the present invention. The absorbing layer can be made rigid, electrically insulating with absorbing capabilities ranging from about 0% (full transmittance) to as much as about 100% absorption (full absorption). For example a transparent layer 35 can be attached to the absorbing layer between the absorbing layer and the light source or lamp. Said absorbing layer can comprise for example a high temperature glass or plastic material doped with absorbing material. Alternatively it can comprise a metal layer capable of absorbing the flash lamps light and also coated with an optically transparent and electrically insulating layer between said metal layer and the flash lamp assembly.

FIG. 4 further shows a preferred embodiment of absorbing layer possible composition, wherein the high absorbing film 23 between the lamps 15 and the skin surface is made of partially transmitting material, for example, part of the film contains high absorbing substance 31 to absorb the light of the lamps, while other portion 33 of the film allows at least some of the optical energy to penetrate through to the skin. This configuration will allow part of the light energy to be converted into heat at the skin surface and directly heat the top layers of the skin, while some of the light is allowed to propagate to deeper skin layer where a gradual absorption by skin cell heats up deeper skin tissue. In addition, some of the light that penetrates deeper skin tissue may be preferentially absorbed by skin components (for example blood vessels, or pigmentation) that may be targeted for destruction or alteration. The device in this embodiment can, therefore, serve for both skin surface treatment as well as targeting of deeper layers skin conditions.

Figure 5:
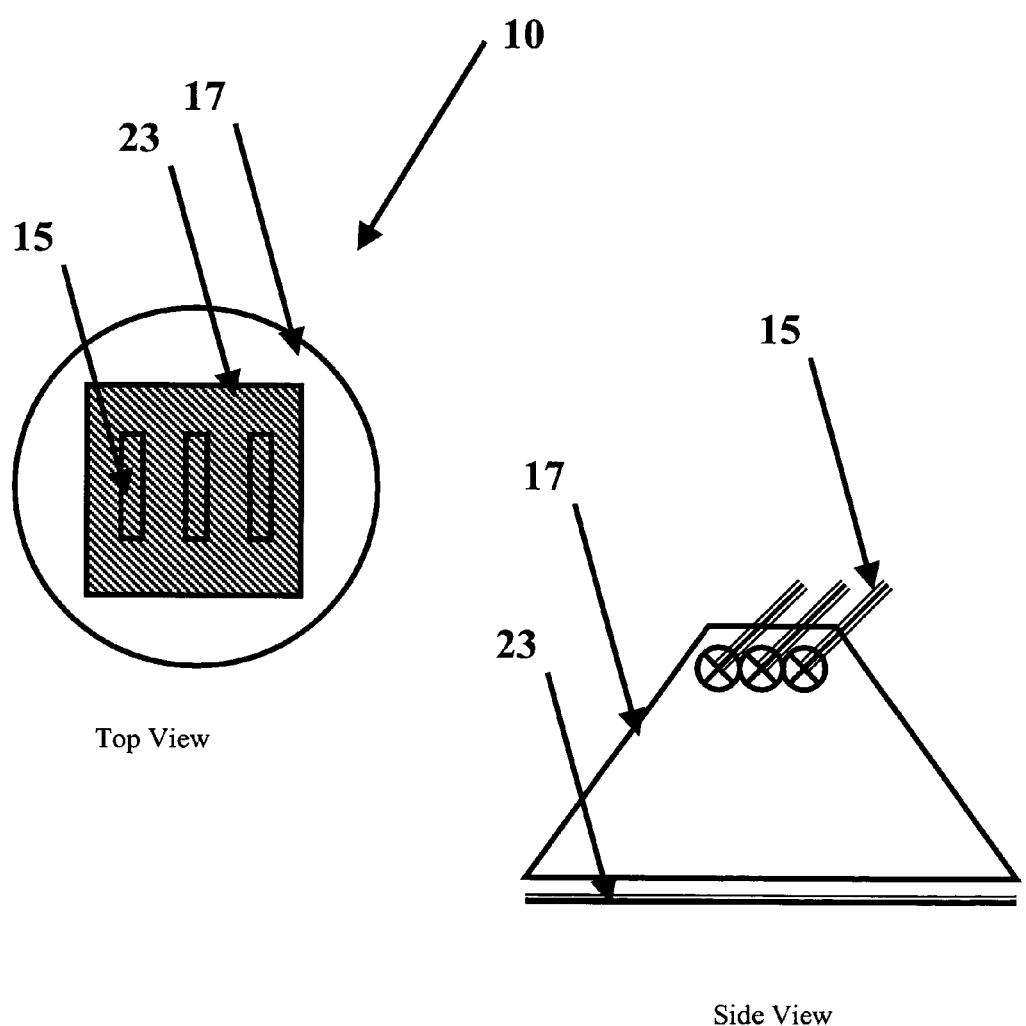
FIG. 5 shows a sectional view taken through the handheld acne treatment device that utilizes flash lamps as an energy source, reflectors, and an optical absorber to deliver energy into the skin. Multi-lamp system is shown.

FIG. 5 shows an alternative embodiment of a skin treatment head 10. In this embodiment, a single reflector 17 encloses a plurality of lamps 15 thus allowing increased energy output from each reflector 17 in the treatment head 10. In this example, each reflector has three lamps. Layer 23 is an absorbing layer.

Figure 6:
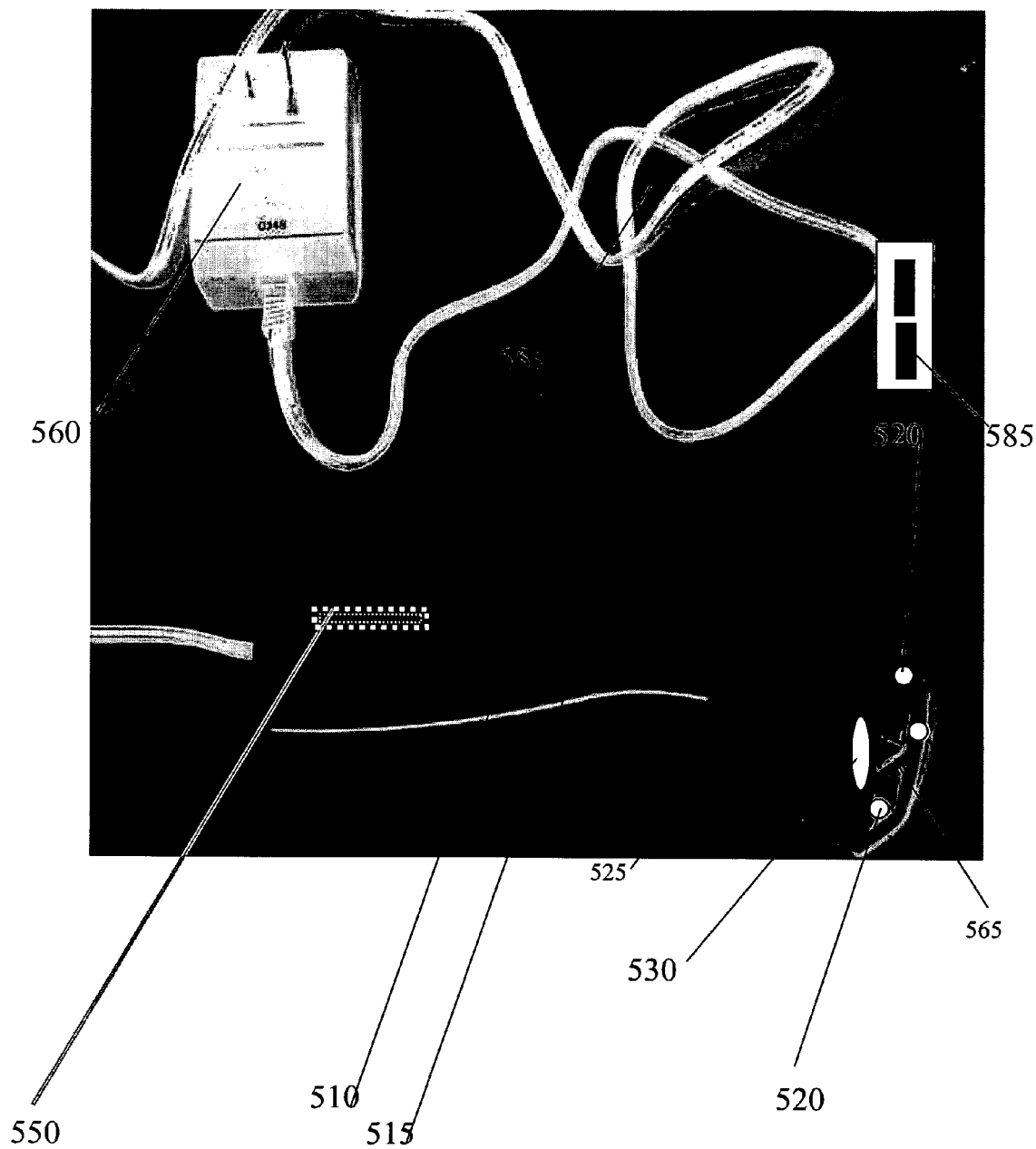
FIG. 6 shows an exploded view taken through an embodiment illustrating one preferred embodiment of a handheld acne treatment device with flash lamps light source, electrical transformer source, and a high absorbing intermediate layer.

FIG. 6 shows another preferred embodiment showing the possible composition of a device for treating Acne and various other skin conditions. The encasing 510 can be made of plastic or metal or other suitable materials and has a handle 515, for example with an approximate diameter of from about 1 cm to about 5 cm and preferably about 2.5 cm in diameter. The handle can also contain a wire connection 555 to a wall plug or a transformer 560 as shown, or a battery 550. The handle may also contain a control board, an off on switch, and capacitors. The treatment head 520 can also be made of plastic or metal material, or other suitable materials The treatment head has treatment windows 565 as discussed above and may also contain LED sources 520 with appropriate wavelength for example for wound healing, bio-stimulation, reduction of acne bacteria, sterilization, skin and collagen rejuvenation, or reduction of pigmented lesions. The treatment head 525 may also comprise a laser source 530 for cosmetic and skin treatments. With appropriate selection of wavelength and intensity and optical diffraction elements such a laser source can be used to treat acne, skin rejuvenation, wrinkle reduction, pigmented lesion and discoloration and reduce the presence of hair on the skin. An opto-thermal converter element 585 may be attached or swung or placed to the front of the treatment head 525 in front of the treating window 565 to provide a surface thermal interaction by converting light from the treatment windows 565 to heat by use of the converter 1310 and 1320 (see FIG. 3) with substance capable of partial or complete absorption of the light from the plurality of light sources.

In another preferred embodiment the system comprises an electronic flash units (often called photographic strobes) which based on the same principles of operation whether of the subminiature variety in a disposable pocket camera, high quality 35 mm camera, compact separate hot shoe mounted unit, or the high power high performance unit found in a photo studio 'speed light'. All of these use the triggered discharge of an energy storage capacitor through a special flashtube filled with xenon gas at low pressure to produce a very short burst of high intensity white light. Such bursts are often on the order of a millisecond. In the present invention we contemplate a pulse duration from about 0.01 ms to about 1 seconds and preferably from about 0.3 ms to about 0.3 seconds and most often on the order of about 1 ms to about 100 ms.

The typical electronic flash consists of four parts: (1) power supply, (2) energy storage capacitor, (3) trigger circuit, and (4) flashtube.

An electronic flash works as follows:

1. The energy storage capacitor connected across the flashtube is charged from a 300V (typical) power supply. This is either a battery or AC adapter operated inverter (pocket cameras and compact strobes) or an AC line operated supply using a power transformer or voltage doubler or tripler (high performance studio 'speed' lights). These are large electrolytic capacitors (100 to 1000+uF at 300+V) designed specifically for the rapid discharge needs of photoflash applications. Such rapid discharge is suitable to the working of the present invention because the device converts such optical discharge into thermal energy at the surface of the skin. Such rapid deposition allows determination of a known quanta of energy to be deposited on the surface of the skin and a known short deposition time. These two elements prevent excess energy from diffusion into deeper tissue area and unwanted collateral damage.

2. A 'ready light' indicates when the capacitor is fully charged. Most monitor the voltage on the energy storage capacitor. However, some detect that the inverter or power supply load has decreased indicating full charge.

3. Normally, the flashtube remains non-conductive even when the capacitor is fully charged.

4. A separate small capacitor (e.g., 0.1 uF) is charged from the same power supply to generate a trigger pulse.

5. Contacts on the device shutter close at the instant the shutter is fully open. These cause the charge on the trigger capacitor to be dumped into the primary of a pulse transformer whose secondary is connected to a wire, strip, or the metal reflector in close proximity to the flashtube.

6. The pulse generated by this trigger (typically around 4-10 KV depending on the size of the unit) is enough to ionize the xenon gas inside the flashtube.

7. The xenon gas suddenly becomes a low resistance and the energy storage capacitor discharges through the flashtube resulting in a short duration brilliant white light.

The energy of each flash is roughly equal to $\frac{1}{2}*C*V^2$ in watt-seconds (W-s) where V is the value of the energy storage capacitor's voltage and C is its capacitance. Not quite all of the energy in the capacitor is used but it is very close. The energy storage capacitor for pocket cameras is typically 100 to 400 uF at 330 V (charged to 300 V) with a typical flash energy of 10 W-s. For high power strobes, 1000 s of uF at higher voltages are common with maximum flash energies of 100 W-s or more. Another important difference is in the cycle time. For some battery operated devices, it may be several seconds—or much longer as the batteries run down. Larger devices or transformer-powered devices, the speed can be a fraction of second cycle times which are common.

In some preferred embodiments the user, usually a skin care professional or a physician, may want to be able to heat up the skin epidermis AND dermis, beyond collagen denaturation temperature. In such cases, a rapid succession of light pulses may be desired. Here the invention contemplates using a common camera feature may be use in such cases. For example, the red-eye reduction feature provides a means of providing a flash twice in rapid succession.

The invention contemplates using a variety of repetition rates depending on the needs. For consumer use, a slower repetition rate is contemplated to avoid pulse-to-pulse thermal build up. However, in professional or physicians use a higher repletion rate is contemplated, to allow, for example, sufficient energy build up in the target tissue so that so that the epidermis is heated for example to a depth of mid reticular dermis and to a time duration that results in permanent denaturation of the collagen, to allow skin rejuvenation and wrinkle reduction.

In this preferred embodiment, the invention contemplates that the main flash would require sub-second recycle time which is not a problem if an energy conserving flash is used. However, it would add significant additional expense otherwise (as is the case with most cameras with built in electronic flash). A separate little bulb is effective and much cheaper.

In another preferred embodiment, an automatic exposure control electronic flash units may be used. Here, automatic electronic flash units provide an optical feedback mechanism to sense the amount of light actually reaching the targeted tissue. The flash is then aborted in mid stride once the proper exposure has been made. This means that the flash duration will differ depending on exposure—typically from 1 ms at full power to 20 microsecond or less at lower power levels.

The invention describes a device and a method for treating a target surface, in particular a skin surface, and the condition of acne, comprising the steps of a) activating an energy source, b) bringing an energy transporter element into contact with the energy source, c) allowing said energy transporter element to absorb some of the energy from the energy source, d) disconnecting said energy transporter and moving it into contact with a target surface, e) allowing a predetermined amount energy from said energy transporter to be transferred to the target surface so that a desired effect is achieved. The method further envisions that the target surface is a biological tissue, in particular skin tissue, and the desired effect is a physical, chemical or biological effect.

The method further envisions a desired effect which is a thermal change in the target surface characteristics.

In yet another preferred embodiment, an energy source creates thermal energy deposition on the surface of the skin to alleviate skin conditions. In further elaboration of this effect the thermal energy deposition alleviates acne conditions. It is possible to alleviate such acne condition for example, by creating expansion of the skin surface so that pores and pore openings are enlarged, allowing drainage of puss, sebum and other undesired material, or even the expulsion of black heads.

The device and method described herein also envisions a preferred embodiment wherein the desired effect of the thermal expansion of the skin surface will allow opening of the skin pores so that said expansion allows at least some enhancement of material or substances to be transported across the skin barrier through spacing between various skin components and through the pores in the skin and the skin surface.

In yet another preferred embodiment, a device for thermal material conditioning is envisioned, wherein said device comprises a heat source which is elevated to the desired temperature and maintained at said desired temperature, means to transporting said thermal energy or heat, such as a heat shuttle in contact with the heat source so that thermal energy can diffuse from the heat source and maintain said heat shuttle at the same temperature as the heat source. The device preferably also includes a trigger that allow an operator to willfully release the heat shuttle from contact with the heat source and bring it into contact with the target treatment area so that thermal energy can flow from the heat shuttle to the targeted treatment material. The device allows said heat shuttle to maintain contact with the targeted treatment area of the target material for a period of time sufficient to bring the target material and the heat shuttle into thermal equilibrium so that substantially no heat flows from the heat shuttle to the targeted material. The heat transporter can then be removed from contact with the skin or other target surface and brought back into contact with the heat source so that it is reloaded with thermal energy.

In yet another preferred embodiment, the transporter of thermal energy or heat shuttle is allowed to maintain contact with the targeted material area for a period of time from about 0.1 microsecond to about 1 second. Similarly, the heat source is allowed to deliver heat to the skin surface for a period of from about 0.1 microsecond to about 1 second.

In another embodiment, the thermal energy source is allowed to deliver a quanta of energy to the surface of the skin in such a way that it brings the skin surface to a temperature of between about 45 degree C. and 500 degree C., preferably, however, the temperature of the surface of the skin reaches between about 50 degree C. and about 350 degree C.

The invention further envisions a preferred embodiment, wherein the device will bring the target material surface (preferably the a skin surface) to a temperature that results in expansion of the skin surface and wherein said expansion of the skin surface will result in at least a 1 micrometer expansion of the pore diameter size. In another preferred embodiment, the steps described above of a device or a method for treating skin conditions utilize an energy source which loads an energy transporter with thermal energy (and increases said transporter's temperature to a desired temperature) then bring said energy transporter into contact with the skin so that the thermal energy may be deposited within the skin (with a desired time duration and desired amount of energy transported within said time duration), this is repeated multiple times at a repetition rate of between about 0.1 Hz and about 1 KHz and preferably between 0.2 Hz and 10 Hz.

In further preferred embodiments, the device and method described about envision utilizing electrical energy as an energy source. Further embodiment envisions the energy source as a thermal energy source wherein the heat source is a thermoelectric cooler. Further preferred embodiment envisions the energy transporter as a heat shuttle made of metal. Said metal heat transporter may also be made of a thin metal sheet of between about 1 micrometer in thickness and about 10 mm in thickness and preferably between about 70 micrometer and 400 micrometer.

Alternatively, and in a preferred embodiment, said heat source is an electric energy source, for example, an electric wall outlet, an electric wall outlet with a transformer, a battery, or a battery and capacitor combination, wherein said electrical energy is brought through the energy transporter (for example, electric wires or metal plates) into contact with a the target surface or skin, where they deposit energy in the form of thermal energy. For example, a metal electric resistor or most materials with inherent electrical resistance may serve for such a purpose. Additionally, a thermoelectric cooler may serve to convert electrical energy into heat with the added benefit of being easily switchable to cooling the target surface after the thermal energy deposition phase. Preferably said electric energy is pulsed so that electric energy, which is then converted to thermal energy which is deposited into the skin surface, is also pulsed. Such pulsed energy deposition phase should last between about 0.1 microsecond and about 100 seconds and preferably, between about 1 ms and about 1 seconds.

In a further version of the present invention preferred embodiment, a device for skin conditioning comprises a heat source wherein a heat shuttle makes contact with said heat source, a console containing both the heat source and the heat shuttle, a transfer compartment capable of separating the heat shuttle from the heat source. The treatment process includes transferring the heat shuttle into contact with the target material, keeping the heat shuttle in contact with said target material for a predetermined period of time, and then removing the heat shuttle from the target material and transferring it back into contact with the heat source. The process can then be repeated multiple times.

A device is capable of repeatedly and automatically heating a target material by bringing an movable component into contact with a high temperature source, by keeping the heat shuttle in contact with a heat source, a. moving the heat shuttle away from the heat source and into contact with a target material to be heated, b. maintaining contact between the heat shuttle and the target material for a predetermined length of time, c. removing the heat shuttle from the target material and brining it back into contact with the heat source and repeating said steps for a predetermined period of time or a predetermined number of repetitions. In some preferred embodiments the device interacts with a target material which is the skin.

The device of the preferred embodiment further envisions bringing the heat transporter into contact with the skin target material for a sufficiently long time to allow expansion of the skin so that at least one skin pore expands and opens enough to allow enhanced material transport through said at least one skin pore. Alternatively, the heat from the source is allowed to be transferred into the skin for a limited amount of time, sufficient to deposit enough thermal energy into the skin allow expansion of the skin so that at least one skin pore expands and opens enough to allow enhanced material transport through said at least one skin pore. In this embodiment the thermal energy source can deposit its energy either by direct transport or conduction into the skin or through the action of an intermediate heat transporter.

Further embodiment of the present invention envisions a device for treating material conditions comprising, a thermal energy source, a heat shuttle in contact with said heat source said heat shuttle comprises a body capable of loading up with thermal energy and two latches, One latch is connected to a spring which tend to propels the heat shuttle towards the target material and keeps it in contact with said target material, The second heat latch is picked up (hooked to) by a rotating motor which propels the heat shuttle back up and brings it back into contact with the heat source. The latch is constructed with a slop so that the rotating motor eventually slips off it allowing the now compressed spring in constant contact with latch number one to propel the heat shuttle again into the target material. The process is repeated until the operator stops The above can also be envisioned wherein the role of the spring and the motor is reversed, i.e., the motor is the one pushing the heat shuttle into the target material and the spring tends to drive the heat shuttle away from the target material and into contact with the heat shuttle.

In further preferred embodiment, the device for material conditioning comprises a magazine full of spring loaded individual heat transport elements (much like bullets are packed into a magazine of a automatic machine gun or rifle magazine such as the military M 16 or Uzi submachine gun). The heat shuttle "bullets" comprise at least thin aluminum plate to be loaded with heat energy and two latches. The latches should be made of non-thermally conduction material or at least a discontinuing between metal part so that said thermal energy remains substantially confined to the heat shuttle. It also includes a spring pushing against one latch in order to allow it to create a good thermal contact with the heat source, a motor driving against the other latch to push the heat shuttle down away from the heat source and into contact with the target material, a remover arm pushing the spent heat shuttles (whose thermal energy was used) away from the device and disposing of them), a loader arm pushing the "bullets" heat shuttles into place where they can be picked up by the spring loading mechanism and be pushed into contact with the heat source.

A motor is used to drive a piston up against a spring (spring loading mechanism). The spring discharge after a stop at the station that allows it to load up with thermal energy. The shuttle is thus propelled by the spring towards the target material to be treated.

The amount of heat energy that was loaded up into the shuttle is finite, so the amount of heat or thermal energy that is discharged into the target material is finite as well. The methods and devices described below contemplate incorporating various thermal energy sources to achieve the desired skin surface effect of temporary but biologically significant expansion so that trans-dermal transport is possible and indeed enhanced. To achieve this effect the thermal energy source can be optical, chemical, or electrical. In all embodiments, the source is to produce sufficient amount of energy which is then to be delivered to the skin surface for only a limited amount of time so that no collateral damage is to result, the expansion is temporary and does not result in any burn to the skin and the source of energy flow into the target skin is cut off at the end of a predetermined time interval so that only a predetermined amount of energy is allowed to be deposited into the skin.

Such design of these preferred embodiments in combination of the relatively slow thermal energy diffusion within the skin, allows concentration of sufficient energy in the upper layer of the skin to enhance transport properties but does not allow sufficient amount of energy to penetrate below the epidermal/dermal junction so that substantially the dermis remains free of burns or any undesirable effects.

One such preferred embodiment envisions the use of electric energy as heat source. In this case, the flow of electrons through a substance with inherent resistance results in joule or resistive heating (one such example will be an electric wire, another is a hot soldering iron). A heat shuttle can then be brought into contact with such electric-energy based heat source and then shuttle the energy into contact with the target material. Alternatively, said electric heat source is connected directly with the target material or skin via conducting material that serves to shuttle the heat and electric energy and the source energy is cut off after a predetermined time. For example, the source of energy can be a full charged capacitor that is connected to the skin via conducting transporter (for example metal wires or metal plates), the capacitor is then allowed to discharge its energy into the energy transporter that is in contact with the targeted skin surface.

Further embodiment envisions a method for Material Conditioning comprising of: a heat source brought to a desired temperature and maintained at that temperature, a heat shuttle (HS) maintained at the source temperature through thermal contact with the heat source, means to willfully trigger said heat shuttle (HS) motion so it is released from thermal contact with said heat source and is brought into thermal contact with the targeted treatment area, allowing said heat shuttle to maintain contact with the treatment area for a period of time sufficiently long to transfer sufficient thermal energy to the targeted region to cause thermal expansion of the treated area and bring about the desired effects including the treatment of skin conditions. Removing the HS from contact with the targeted area and bringing it back into thermal contact with the heat source The method above further contemplates a contact period between the heat shuttle and the treatment area is from about 0.1 ms to about 1 second and preferably from about 1 ms to about 100 ms (In water-like material such a period of 100 ms will allow thermal energy to diffuse to roughly a depth of penetration of about 300 um). The method of further comprises repeating all steps at the repetition rate of between 0.1 Hz and 1 KHz and preferably at a repletion rate of between 0.2 Hz and 10 Hz. In further elaboration of this embodiment, the heat source is powered by electrical heater driven by electrical energy. In yet further possible embodiment of the present invention, the heat source is a thermoelectric cooling device (TEC) or Paltrier cooling device. Additionally, the heat shuttle can be made of thermally conducting material. In yet another preferred embodiment, the heat shuttle (HS) can be made of metal.

An additional embodiment envisions the heat shuttle as made of metal of sufficient contact area with the target material to allow reasonable work rate and preferably a contact area with the target material of between about 0.2 cm2 and about 4 cm2.

In a further preferred embodiment, the method and device of the present invention contemplate a heat shuttle made of metal of sufficient volume and heat capacity to allow the heat shuttle to carry thermal energy sufficient to raise the temperature of the upper layers of the skin to cause the desired effect and in particular to improve or cure undesired skin conditions. Additionally the heat shuttle (HS) may be made of thermally conducting material in the form of a sheet with a thickness of between about one micrometer and about one millimeter in thickness and preferably between 70 micrometer and 200 micrometer, so that the desired biological effect is achieved.

For example, in a preferred embodiment the target material is the skin and sufficient thermal energy is delivered by the heat shuttle to the targeted skin to cause thermal expansion of the skin in the treated region and opening of the pores in said skin region to allow substance to flow in or out of at least a portion of the skin through at least some layers of the epidermis.

The present invention further contemplates a device for material conditioning, and in particular for treating skin conditions, comprising:
a) A heat source;
b) A heat shuttle in contact with said heat source;
c) A console to contain both the heat source and the heat shuttle (HS) and to ensure that neither is in thermal contact with the target treatment area during at least part of the device operation time;
d) A transfer element capable of separating the heat shuttle from the heat source and brining it into contact with the target material keeping the heat shuttle, keeping the heat shuttle in contact with said target material for a predetermined period of time then removing the HS from the targeted material and bringing the HS back into thermal contact with the heat source. This device for material conditioning should also be capable of repeatedly and automatically heating a target material by heating a heat shuttle (HS) by keeping it in contact with a heat source, moving said heat shuttle away from the heat source and into contact with the target material, keeping the HS at the target material for a predetermined period of time, removing the HS from the target material and bringing it back into contact with the heat source, repeating said steps at a predetermined repletion rate for a predetermined total operation time period. The device of this embodiment should further comprise keeping the heat shuttle in contact with the target material for a sufficiently long time to allow thermal expansion of the target material.

The device of this embodiment also contemplates that the target material is skin and the heat shuttle is kept in contact with the skin for a sufficiently long time to allow thermal expansion of the skin and opening of the pores in said skin region to allow substance to flow in or out of at least a portion of the skin through at least some layers of the epidermis.

The present invention further contemplates a device for material conditioning capable of repeatedly and automatically heating a target material by heating a heat shuttle (HS) by keeping it in contact with a heat source and moving said heat shuttle away from the heat source and into contact with the target material, keeping the HS at the target material for a predetermined period of time, removing the HS from the target material and bringing it back into contact with the heat source, repeating said steps at a predetermined repletion rate for a predetermined total operation time period. The present device further contemplates keeping the HS in contact with the target material for a sufficiently long time to allow thermal expansion of the target material.

In further elaboration of this embodiments, the target material is skin and the heat shuttle is kept in contact with the skin for a sufficiently long time to allow thermal expansion of the skin and opening of the pores in said skin region to allow substance to flow in or out of at least a portion of the skin through at least some layers of the epidermis. The device further comprises a pump to lower the pressure within the device chamber and create a tighter seal to the skin. This will allow: better contact with the skin, removal of debris from the skin and pores, and reduction of the amount of air within the chamber in order to minimize heat conduction and heat removal from the HS during it passage from the heat source to the targeted skin. This embodiment further envisions the device comprising generating lower pressure through a pump.

The present invention also contemplate coating the heat shuttle of the above embodiments with nutrients, drugs, medications or any other substance that is desirable to deliver into the target surface. Furthermore, the device of any of the above embodiments contemplate such nutrients, medications, or drugs or any other substance is applied to the same area of the skin before, during, or after the action of the heat shuttle. The present invention further contemplates the device of any of the above embodiments, wherein, a container and dispenser containing and dispensing a drug or any other substance that one wishes to deliver into the target surface is attached to the heat shuttle apparatus and delivery a desirable substance before, during or after the action and passage of the heat shuttle.

Figure 7:
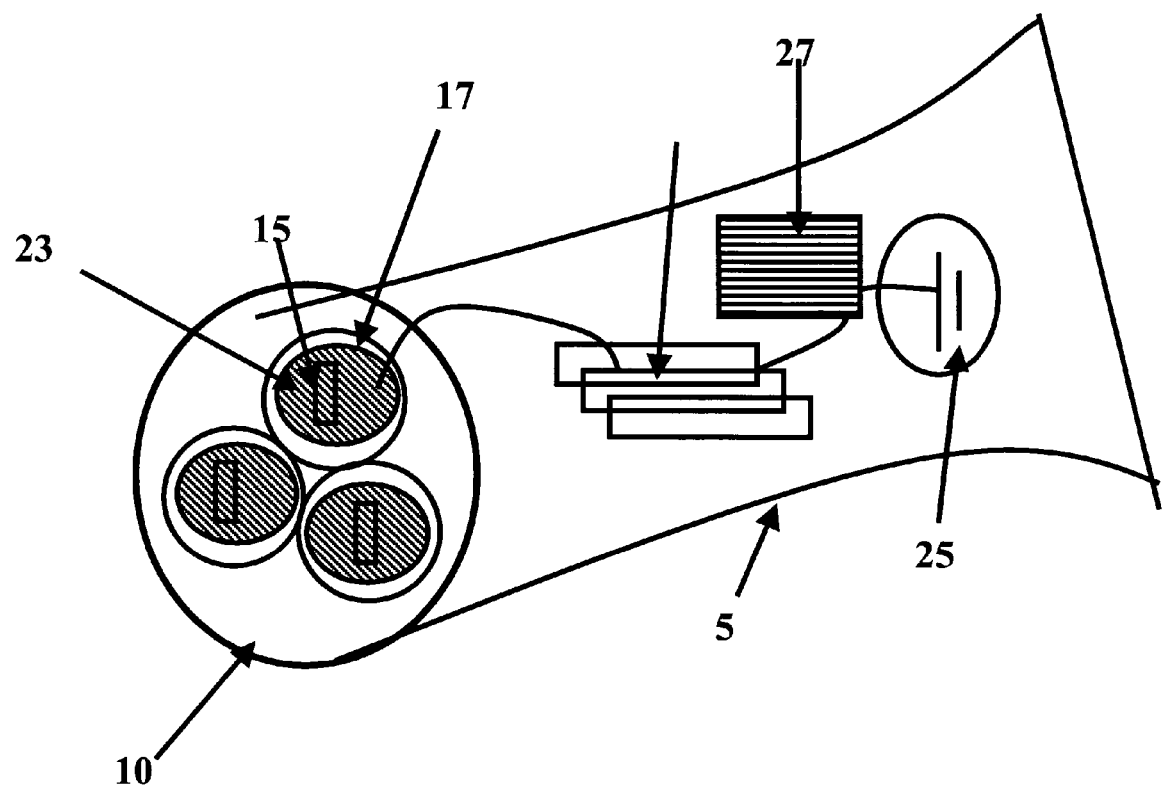
FIG. 7 shows a sectional schematic view taken through another embodiment of the hand-held acne treating device.

FIG. 7 illustrates the general configuration of a light-based device for skin rejuvenation. A plurality of flash lamps 15 are placed at the treating end (treatment head) 10 of a handheld device 5. The treatment heads deliver a predetermined amount of optical energy. The amount of energy is determined by the discharge energy of a plurality of capacitors 20 powered by an energy source 25, such as a plurality of batteries or any other energy source 25.

Each flash lamp 15 is placed inside a reflector 17 and its optical energy is absorbed and at least partially converted to thermal energy by a film 23 of high absorbing substance capable of absorbing said optical radiation.

In another preferred embodiment illustrated by FIG. 7, said flash lamps 15 can be fired sequentially to provide a staggered treatment of different area in a desired predetermined sequence.

In yet another preferred embodiment shown in FIG. 1, an auxiliary cooling component 1252 is activated between 0.1 ms and 1 seconds and preferably from about 1 ms to about 100 ms after the light is discharge thus allowing heat flow to the reach the dermis yet spare the epidermis from damage. The cooling component comprise a container 1252 which is used to contain a cooling agent such as, for example, a gas with low evaporating temperature such as an environmentally compatible freon-like fluid. The cooling fluid is transported by a tube 1253 or other means to conduct fluid to a discharge nozzle 1254. The nozzle allow controlled timing of the discharge of the cooling liquid that is directed towards the target to remove heat form the target while evaporating. The discharge control can be achieved, for example, with an electronic fuel injection valve which is well known in the art.

Figure 8:
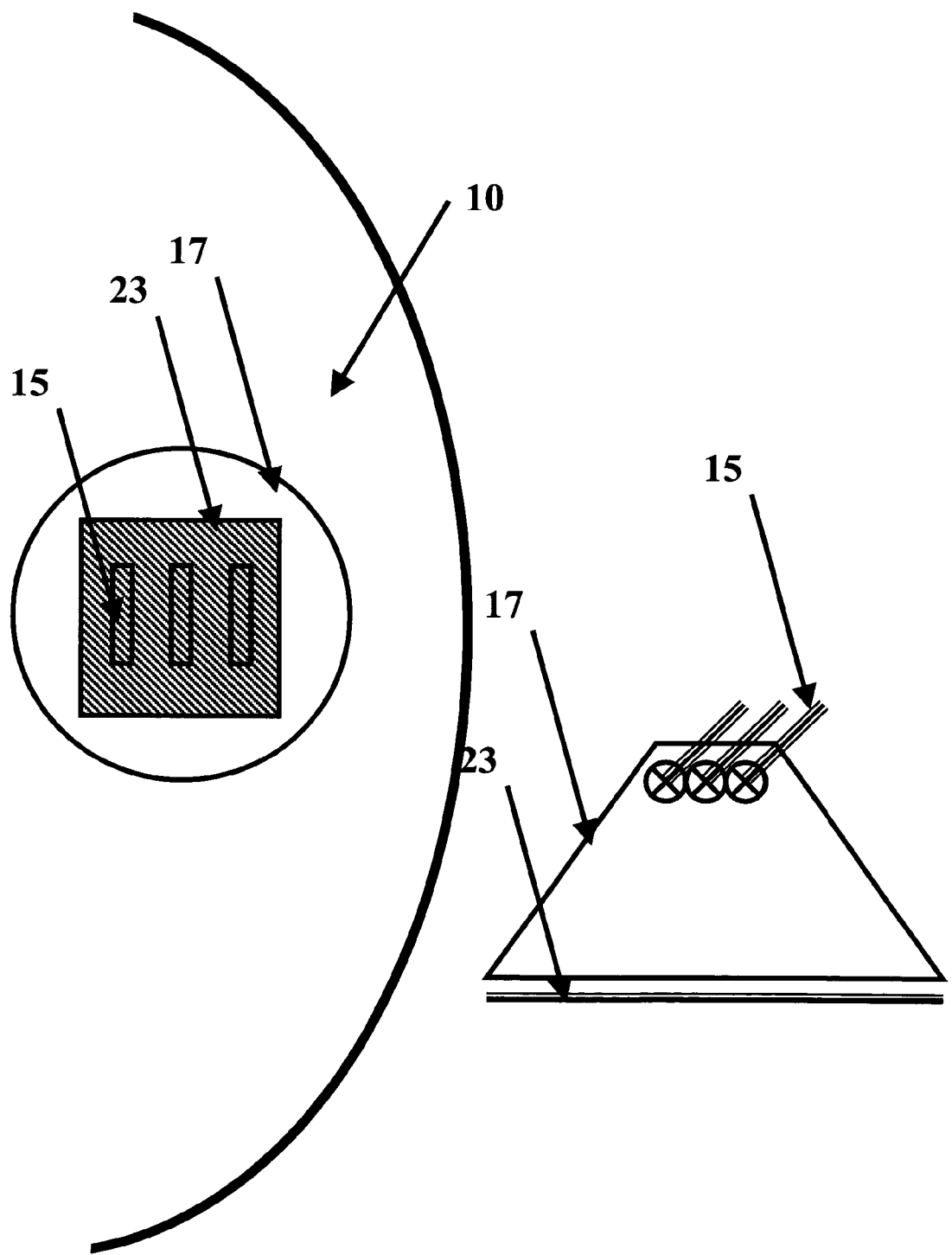
FIG. 8 shows a sectional view taken through another embodiment of treatment head showing both side view and a view from the bottom.

FIG. 8 shows an alternative embodiment of a skin treatment head 10. In this embodiment, a single reflector 17 encloses a plurality of lamps 15 thus allowing increased energy output from each reflector 17 in the treatment head 10. In this example, the reflector has three lamps.

Figure 9:
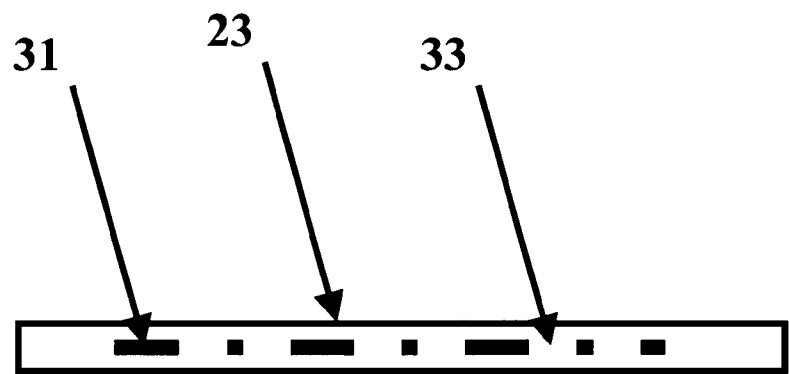
FIG. 9 shows another embodiment of the composition and structure of the high absorbing intermediary layer in the handheld acne treatment device.
Figure 9:
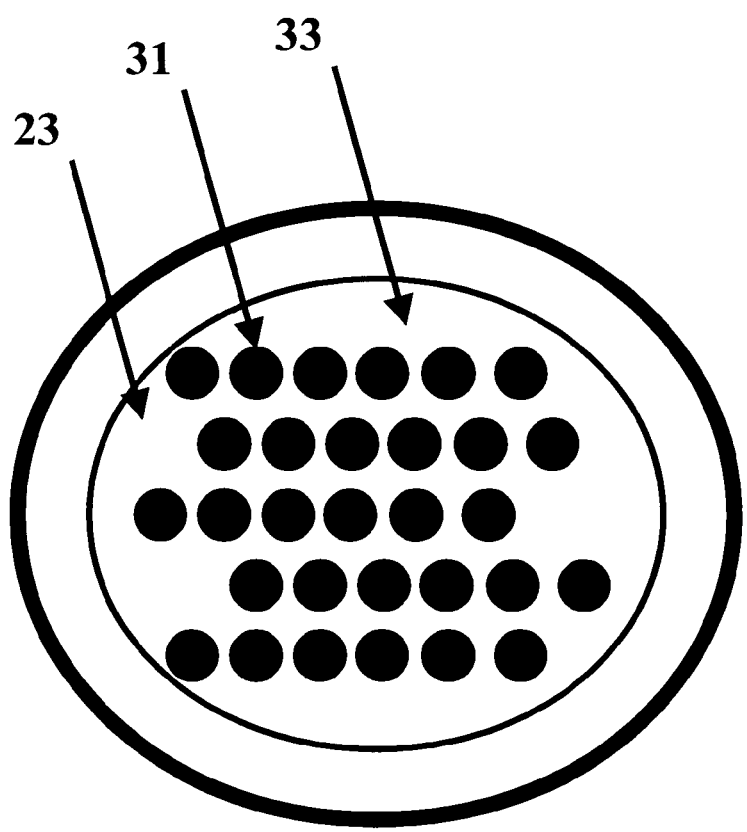

In FIG. 9 yet another preferred embodiment is shown, wherein the high absorbing film 23 between the lamps 15 and the skin surface is made of partially transmitting material, for example, part of the film layer contain high absorbing substance 31 to absorb the light of the lamps, while other portion of the film 33 allow at least some of the optical energy through to the skin. This configuration will allow part of the light energy to be converted into heat at the skin surface and directly heat the top layers of the skin, while some of the light is allowed to propagate to deeper skin layer where a gradual absorption by skin cell heats up deeper skin tissue. In addition, some of the light that penetrates deeper skin tissue may be preferentially absorbed by skin components (for example blood vessels, or pigmentation) that may be targeted for destruction or alteration. The device in this embodiment can, therefore, serve for both skin surface treatment as well as targeting of deeper layers skin conditions.

Figure 10:
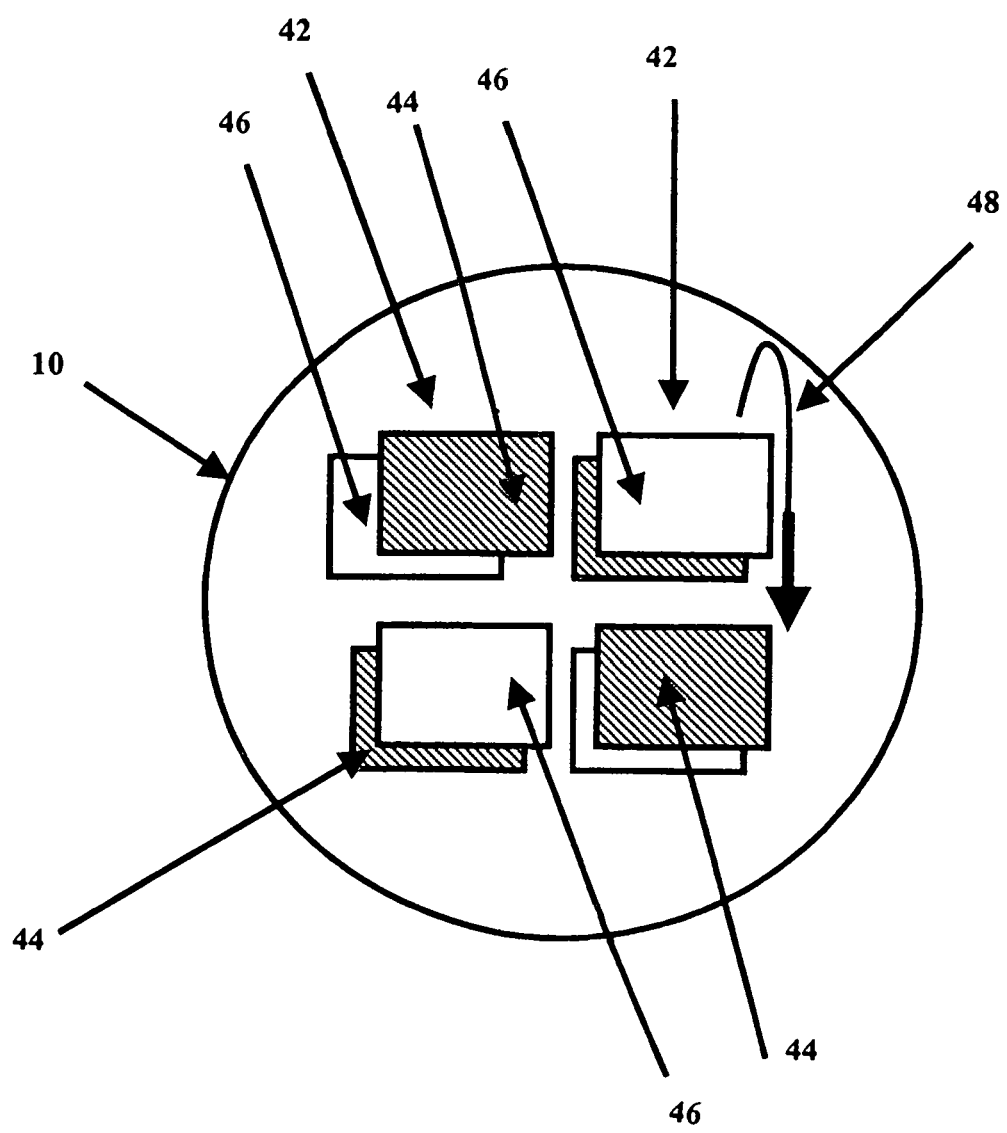
FIG. 10 shows a treatment head of a handheld acne treatment device including multiple-treatment heads of both light with high absorbing intermediate layer as well as optical energy alone.

FIG. 10 shows yet another preferred embodiment of the present invention. Here the treatment head contains a plurality of treatment windows 42. Some of these windows (44) consist of a flash lamp and high absorbing substance (HAS) configuration for opto-thermal skin surface modifications (OTSSM), while some of these windows (46) contain a flash lamp and a transparent window that allows deeper skin light penetration for direct optical energy light treatments. The two types of windows (44, 46) can be mounted on a moving mechanism 48 (for example a conveyer belt type mechanism) in an alternating sequence (for example surface opto-thermal treatment window 44 followed by an optical energy treatment window 46). While the window(s) closer to the skin is/are performing the treatment, the treatment widow(s) further from the skin can be charged for their turn of the treatment. Following the capacitor discharge and the treatment, the moving mechanism 48 can move the treatment windows 42 closer to the skin to the back and those in the back to the front. The treatment can then be repeated while the windows in the back are recharging.

Figure 11:
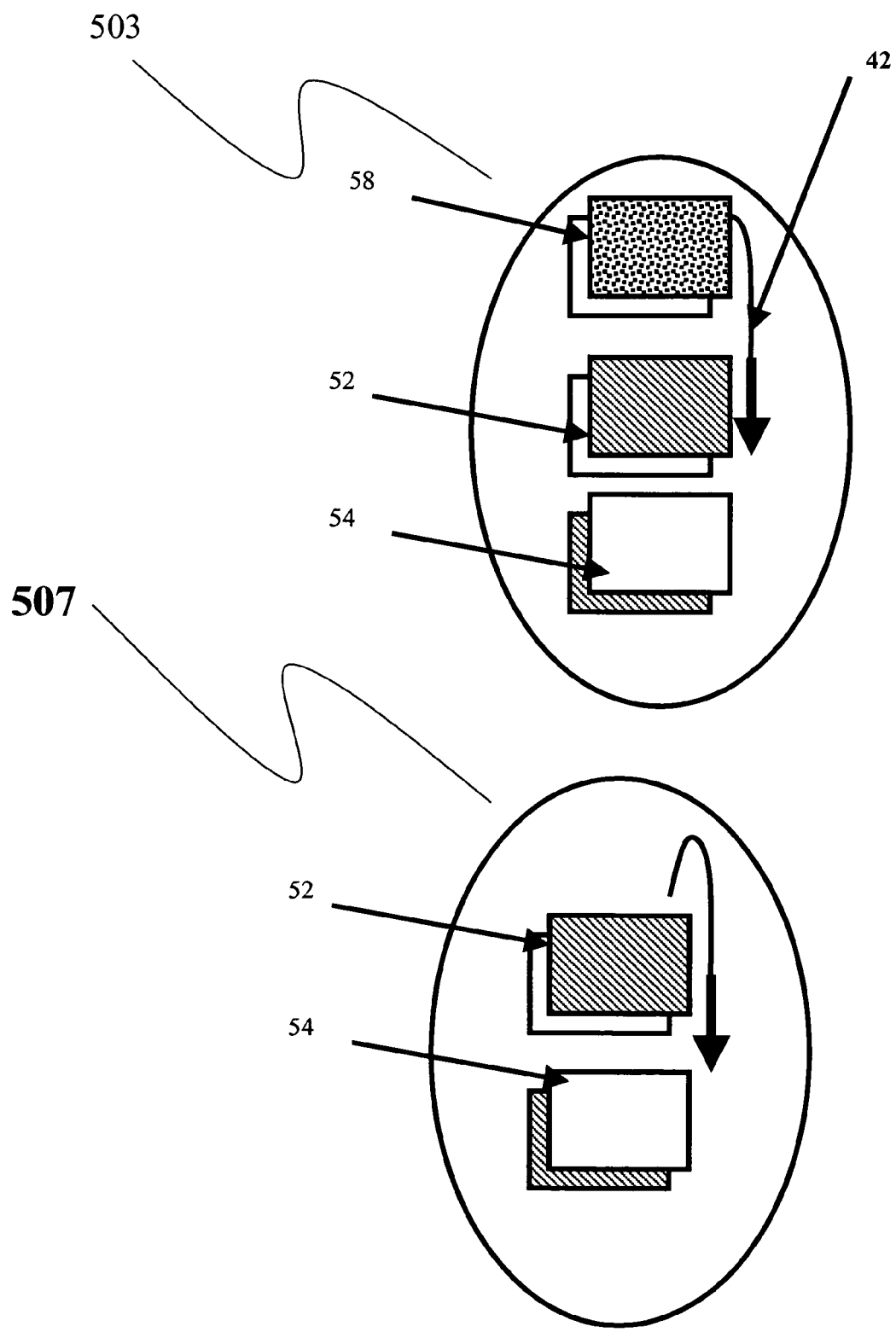
FIG. 11 illustrates two other possible treatment heads configuration utilizing a variety of multiple treatment windows that can be move and replaced within a treatment.
Figure 11:
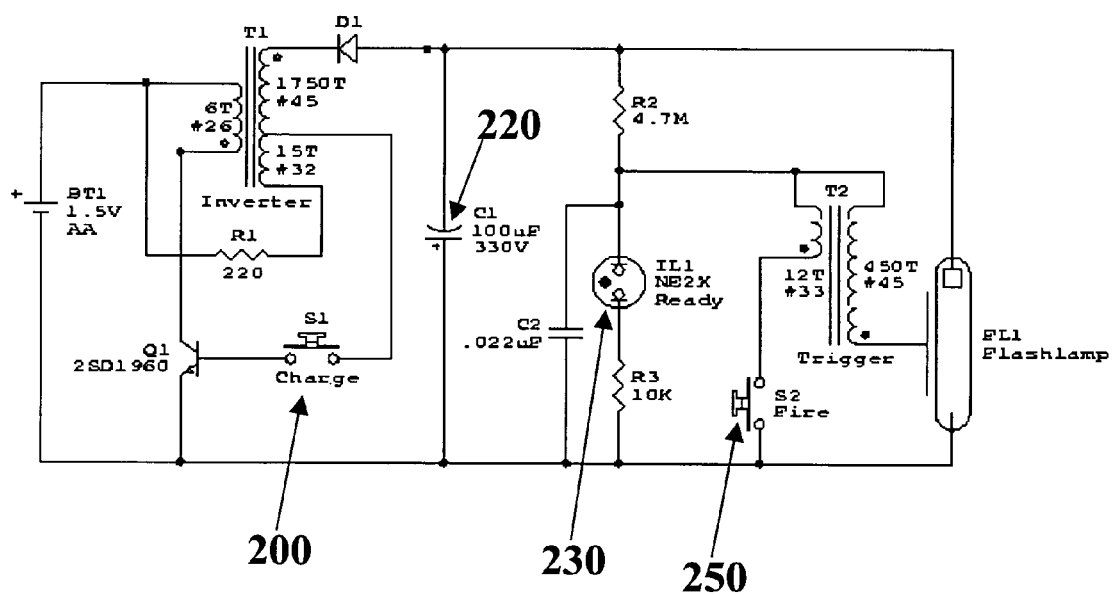

FIG. 11 shows another preferred embodiment wherein the plurality of treatment windows 42 can be made of two (507) or three (503) windows and the treatment windows can be made of flash lamp and high absorbing substance (HAS) combination 52, a flash lamp/optical energy source 54, and an electric heater made of electric resistor for electro-thermal heating alone 58. Such a combination would allow, for example, short and rapid surface heating with the flash lamp/HAS combination, deep tissue heating with the flash lamp, and higher temperature longer heating with the electric resistor.

The main structures are the stratum corneum (a plurality of dead skin cell with a variable degree of adherence to the skin surface). The stratum corneum may vary in thickness but is generally less than 20 micrometer in thickness. Below the stratum corneum lies the epidermis which can reach as much as 150 micrometer in thickness depending on the location of the skin on the human body. Below the epidermal-dermal junction lies the dermis whose thickness is in the millimeter range and can vary considerably depending on the location on the human body. The epidermis contains among other things, blood vessels, the nerve ending living cells, sebaceous gland, hair shafts and the roots and matrix of the body hair, sweat glands, and sweat ducts. Below the epidermis lies a layer of body fat cells.

It is generally accepted today that controlled thermal damage to the upper layer of the dermis (down to as much as 300 micrometer into the dermal layer) results, following a healing process, in production of new collagen with both improved elasticity and tightness. The present invention envisions a plurality of skin improvement effects by the methods of the present invention:

By depositing a controlled amount of thermal energy at the surface and allowing said energy to flow into the upper layer of the dermis, to achieve controlled damage to the collagen in the upper dermal layer. Possibly a cooling element can be activated after a predetermined time of surface heating to, remove thermal energy from the surface of the skin, protect the surface of the skin from a lengthy exposure to thermal energy, and reversing the flow of thermal energy from deeper lying layers in the dermis back to the surface;

By temporarily enlarging skin surface pores and allowing cleaning of the pores and causing expulsion of unwanted debris, dirt and contaminants in the body pores, thus resulting in reduced pore size;

By temporarily enlarging skin surface pores thus allowing nutrients, conditioner, and possibly drugs and medication to flow into deeper layers of the skin;

By temporarily enlarging skin surface pores and allowing the expulsion of harmful sebum and bacteria thus reducing the chance for the development of acne and other sebaceous gland related ailments;

By thermally damaging the surface layers of the skin followed by flaking and removal of portion of the stratum conium, and portion of the epidermis and dermis; By thermally damaging vascular or pigmented component of the skin near the skin surface (in the epidermis or upper dermis). These unwanted damaged components will then be removed by the body as waste products, eliminating disfiguring skin blemishes.

Table 1 shows approximated diffusion times for selected typical distance in water-like media such as the human or animal skin. For example the diffusion of heat to a distance of about 100 micrometer will require approximately 10 milliseconds. These diffusion times ensure that no thermal energy deposited at the surface arrives at deeper skin locations prior to these times. Knowing these approximate diffusion times the present invention contemplates limiting the extent of thermal damage to deeper skin structures by terminating the action of the energy source at the surface and possibly by introducing a skin surface cooling element subsequent to the thermal energy deposition such that the flow of thermal energy is reversed back to the surface and no thermal energy reaches below a predetermined depth.

TABLE 1

| Diffusion Times | Z Depth | Times |
|---|---|---|
| | 1 um | 1 us |
| | 10 um | 100 us |
| | 100 um | 10 ms |
| | 1 mm | 1 sec |

To Calculate the energy needed to increase the temperature of a given volume (Volume=Area*Depth) to a temperature DT is:

$$C = DE/DT \grave{O} DE = C\, DT$$

$$DE = C\, DT = c * Ro * Vol * DT$$

$$DE = c\, Ro\, A * \text{Depth} * DT$$

Specific heat capacity water–4.187 kJ/kgK=C
Hence $$DE = DT \times 4.2 \text{ KJ}/(KG*K)$$

Volume=10 um×Cm2=1E-5×1E-4 m3
Volume=1E-9 m3
Density=Kg/m3
Mass=M=1E-9 Kg
=1E-6 Gram=ug
With DT=100 C $$DE = 4.18 \text{ (kJ/Kg) } 1E\text{-}9 \text{ Kg/K} * 100K = 4.2\, E\text{-}7 \text{ KJ}$$

Hence $$DE = 4.2\; 1E\text{-}7 \text{ KJ} \sim 4\, E\text{-}4J = 0.4 \text{ mJ}$$

Table 2 shows the basis for a design of a system for skin conditioning treatment based on the thermal properties of the skin. The right column shows the required energy to bring a volume of the skin with water-like thermal properties to an increase in temperatures (DT) shown in the left column. The calculations assume a skin volume of a centimeter square and depths reaching those shown in the left column.

TABLE 2

| Parameters (DT, Depth = dZ) in water<br>The area considered in this example is generally about 1 cm2. | DE = energy needed to raise and area of 1 cm2 and of a depth = dZ, To Temperature DT (mJ) | Diffusion time (ms) to allow surface energy to reach said depths |
|---|---|---|
| 100 C., 10 um depth | 0.4 J | 0.1 ms |
| 100 C., 100 um | 4 J | 10 ms |
| 200 C., 10 um | 0.8 J | 0.1 ms |
| 200 c, 100 um | 10 J | 10 ms |
| 100 C., 200 um | 10 J | 40 ms |
| 200 C., 200 um | 20 J | 40 ms |
| 300 C., 100 um | 15 J | 10 ms |
| 300 C., 200 um | 30 J | 40 ms |
| 300 C., 300 um | 45 J | 90 ms |

Table 3 shows the particular energy delivery times of interest in the present invention (ranging from about 0.1 ms to as much as about 90 ms) and corresponding to thermal diffusion depths from about 10 micrometer to about 300 micrometer well into the upper layers of the dermis. As can be seen from the tables, the energy density contemplated by the invention is in the range from about 0.1 J/cm$^2$ to about 50 J/Ccm$^2$2

TABLE 3

| Thermal Diffusion distance (um) | Thermal Diffusion time |
|---|---|
| 10 um | 100 us = ~0.1 ms |
| 30 um | ~1 ms |
| 50 um | 2.5 ms |
| 70 um | 5 ms |
| 100 um | 10 ms |
| 200 um | 40 ms |
| 300 um | 90 ms~0.1 SEC |

Table 4 shows the ratio of thermal expansion that would result from raising the temperature of a water-like material by the additional level shown in the left column. It confirms the present invention assertion that a sufficient volumetric expansion change will result allowing opening of the pores.

TABLE 4

| Volume = 10E−9 m3 = 10E+9 um3<br>Thus DV/V = 700 E−6 * DT<br>@ 100 C.<br>→ DV/V = 0.07<br>To first approximation:<br><br>DV/V~3 DL/L<br>DA/A~2 DL/L | | |
|---|---|---|
| Delta Temp (DT C.)<br>(temp increase) | DV/V (%)<br>Expansion ratio | DL/L % of<br>Linear expansion |
| 100 | 7 | 2.3 |
| 200 | 14 | 4.7 |
| 300 | 21 | 7 |
| 400 | 28 | 9.3 |
| 20 | 1.4 | 0.5 |
| 50 | 3.5 | 1.2 |

FIG. 11b shows another possible circuit diagram to pulse the flash lamp. A switch 200 is turned on to activate the device and charge the capacitor 220. When the capacitor is fully charged a lamp 230 (or LED) turns on and the circuit is ready to fire. Push button 250 is pressed to trigger the flash lamp which discharges capacitor 220. After firing, the capacitor 220 again begins to charge and after several seconds (depending on battery and resistance) is fully charged. This circuit releases a maximum energy per pulse of ½CV$^2$ where C is the capacitor capacitance and V is the final voltage across the capacitor. By selecting appropriate values of C, and V the released energy can be kept below the threshold for tissue burns. The present invention can use any suitable conventional circuit for the above firing process.

Figure 12:
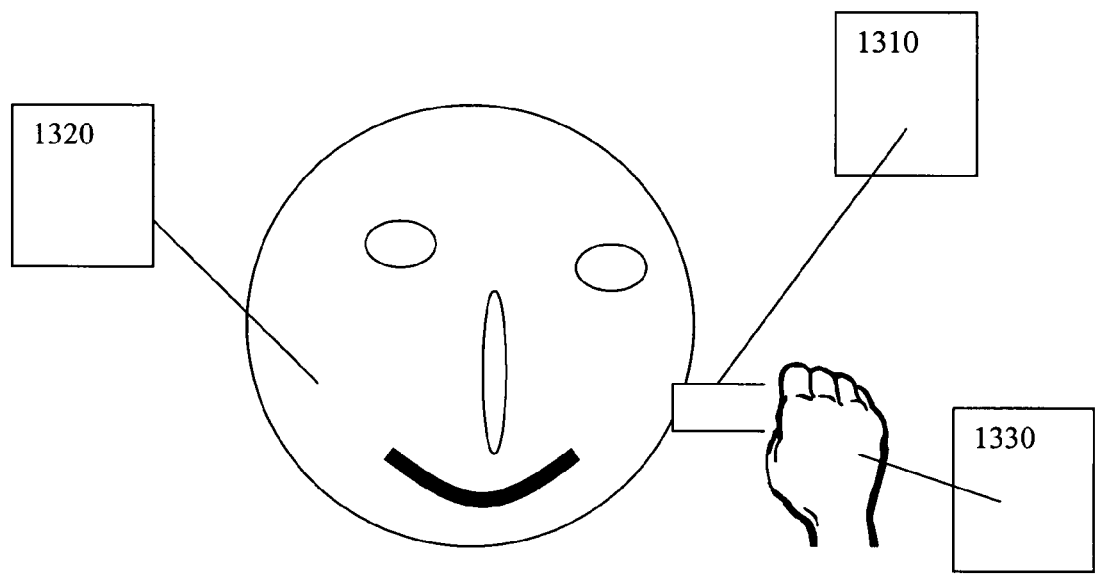
FIG. 12 illustrates how the handheld acne treatment device might be used on the skin of a human face

FIG. 12 shows how the present invention may be used to treat a blemish on the face. The device 1310 is turned on and then placed in contact with the skin 1320, when in good contact and fully charged, the fire button is pressed by the operator hand 1330 to deliver energy to the heating element which then transfer its energy to the skin. The thermal impulse to the skin acts to open pores and accelerate clearing of the blemish.

Figure 13:
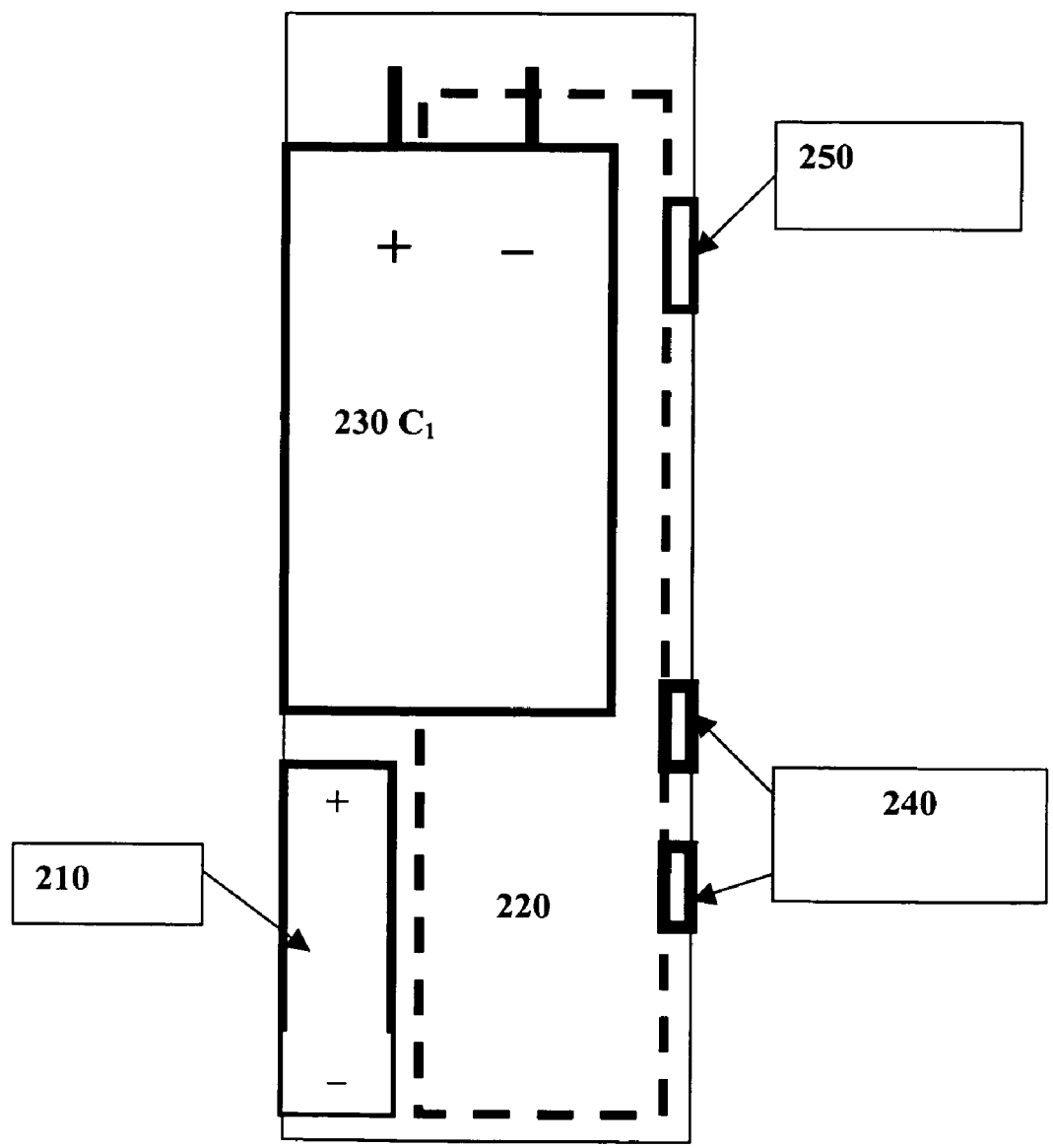
FIG. 13 is a sectional view showing the component of the enclosures of a possible embodiment of the handheld acne treatment device.

FIG. 13 shows the components driving the skin treatment device. They include a power source 210, an electronic control board 220, a capacitor 230 charged with the energy needed, a charge/fire buttons 240 and an indicator light 250 indicating that the charge cycle is completed and the unit is ready to be used.

Figure 14:
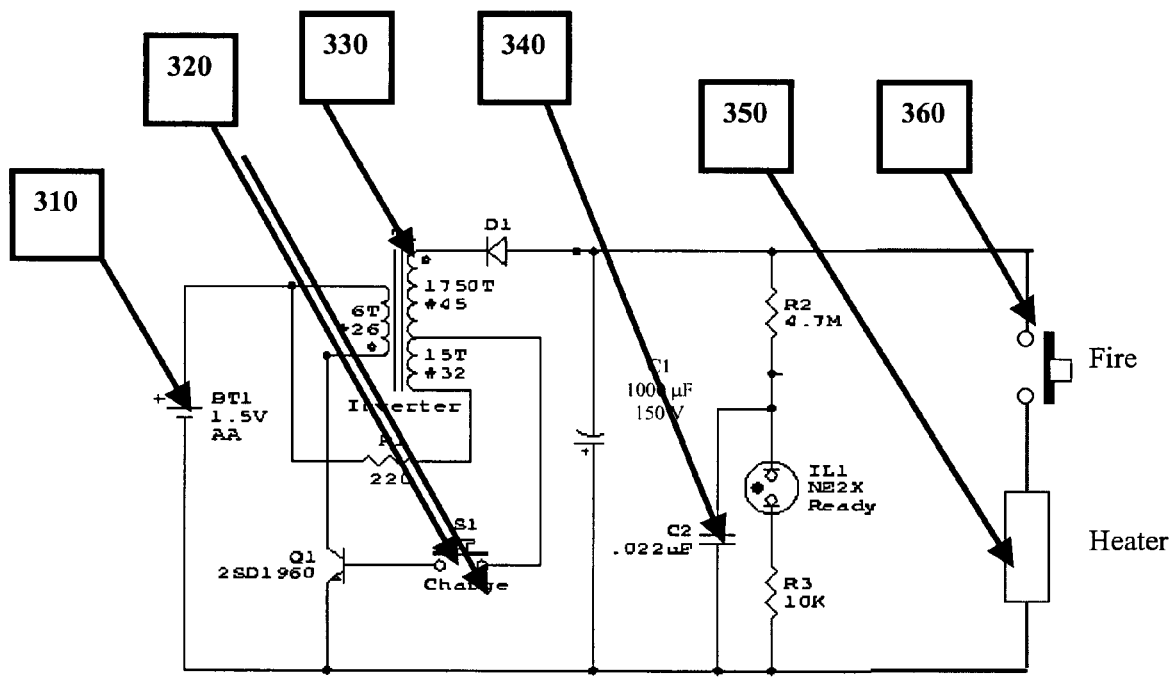
FIG. 14 is a sectional view showing a possible circuit driving an electrical discharge to generate an electric pulse heating of the hand held acne treatment device.

FIG. 14 is a schematic diagram for the circuit needed to drive an electric resistor energy source and transport configuration. A power source (for example a 1.5V or 6 V battery) voltage is stepped up by a voltage inverter 330 and charges a capacitor 340. A switch 320 activates this process. The capacitor 340 is discharge by a push on the fire switch 360 to heat up the electric resistor treatment head 350.

In a further embodiment of the present invention, a device for treating the skin is contemplated, said device delivers a controlled amount of thermal energy to tissue and comprises:
- a flash lamp with an electromagnetic radiation absorbing element,
- a circuit to deliver a fixed amount of energy to said flash lamp,
- a layer of absorbing layer capable of absorbing the optical energy discharged by the flash lamp, a component capable of activating and triggering said circuit. Another preferred embodiment contemplate a device for delivering a controlled amount of thermal energy to tissue comprises an optical absorbing element with variable transmittance properties, at least one flash lamp, a circuit to deliver a fixed amount of energy to said plurality of flash lamps, means to activate and trigger circuit.

The present invention also contemplates a preferred embodiment wherein a method for treating skin blemishes includes a trigger circuit to released a pre-determined amount of energy to a plurality of flash lamps, an absorbing substance capable of absorbing at least some of the light energy and converting it to thermal energy, heating a predetermined upper layer of the skin to a temperature in excess of about 50° C. The method further contemplates that the layer below the epidermal dermal junction remains below 50° C.

In another embodiment of the present invention, the method contemplates keeping the layer below the mid-reticular dermis remain below 50° C.

The present invention also contemplates the possibility of using a cooling element is activated at a predetermined time subsequent to the heating of the skin to remove at least some of the thermal energy from the skin.

Yet another embodiment of the present invention contemplates a device for delivering a controlled amount of thermal energy to tissue comprising:
- an optical absorbing element with variable transmittance properties,
- at least one flash lamp,
- at least one electrical heating element,
- a circuit to deliver a fixed amount of energy to said plurality of flash lamps, and heating elements,
- means to activate and trigger circuit.

The above device also contemplates including an element for dispensing substance beneficial to skin conditioning or skin therapy is activated followed the treatment allowing delivery of said substance into the skin.

Yet another embodiment of the present invention envisions a device for delivering a controlled amount of thermal energy to tissue comprising a resistive heating element, a circuit to deliver a fixed amount of energy to said resistive heating element, means to activate and trigger circuit. This device further includes an element that prevents electrical current from reaching the treated surface. Only the heat energy should be allowed to be transferred into the skin, but no electrical current. This can be accomplished by coating the electric heating element with electrical insulator that prevent electric current flow but allow at least some thermal energy flow.

The present invention further contemplates device for treating skin blemishes including applying a device with an element that can be quickly heated to temperature greater than 50° C. to the skin, triggering a circuit to release a fixed amount of energy to the heated element, allowing heat to conduct into the skin. The device may further comprise an electric insulation which is placed between the resistive heating element and the surface of the targeted skin but which allows thermal energy flow across it.

Further embodiment of the present invention envisions a therapeutic treatment device comprising: an incoherent electromagnetic energy source operable to provide a pulsed energy output from a plurality of energy sources having a spectrum of frequencies including a frequency bandwidth capable of being absorbed by an intermediate substance; a housing with an opening, said light source being disposed in said housing, and said housing being suitable for being disposed adjacent to the intermediate substance; a variable pulse-width pulse forming circuit electrically connected to said light source; a reflector mounted within said housing and proximate said light source, directing its energy towards said absorbing intermediate substance whose absorbing characteristics range from zero (completely transmitting) to infinity (completely absorbing).

The device above is contemplated to have fluence of less than about 2 J/cm$^2$, and in a modification of the above, at less than about 1 J/cm$^2$ Yet another preferred embodiment contemplates the device above with an incoherent energy source which is supplemented with a laser energy directed at the general vicinity of the treatment area before, during or after the application of the pulsed energy output.

Yet another embodiment of the device above contemplates substantially depositing most of the energy of the electromagnetic source is deposited at the surface.

The device contemplated by the present invention described above also envisions that substantially most of the energy of the electromagnetic energy source is deposited at the surface, resulting in expansion of skin surface opening and discontinuities to allow at least some enhancement in the transport of material across the skin to alleviate skin conditions and ailment and to improve the look and condition of the skin.

The embodiment above may also be modified to provide a device with a plurality of energy sources, such as lamps with reflectors with electromagnetic energy output and wherein at least one lamp energy is intercepted by a high absorbing film mounted proximate to the lamp opening.

Further modification of the embodiment above envisions that said energy source is a light source, a flash lamp, or a flash lamp of the type used in digital and disposable (single use) cameras.

Further embodiment envisions the embodiment of the device above wherein said energy source comprises means for providing pulses having a width in the range of between about 0.5 microseconds and 500 millisecond and an energy density of the light on the skin of more than about 0.1 J/cm$^2$ and less than about 2 J/cm$^2$.

Further embodiment contemplates a skin treatment device wherein said energy source comprises means for providing a pulse in the range of about 0.1 milliseconds to 2000 milliseconds, whereby skin opening may be expended to enhance transport across the skin. This device may also have an energy source comprising means for providing pulsed electromagnetic energy in the range of about 0.1 millisecond and about 1000 milliseconds, and providing laser CW light radiation before, during, or after said pulse radiation. This device may also have an energy source that comprises means for providing pulsed electromagnetic energy in the range of about 0.1 millisecond and about 1000 milliseconds, and providing laser CW light radiation before, during, or after said pulse radiation and providing lamp radiation before, during, after, and is able to heat the dermis/epidermis junction temperature to between about 45° C. and 55° C.

The device may also comprise means for providing pulsed electromagnetic energy in the range of about 0.1 millisecond and about 1000 milliseconds, and providing lamp radiation before, during, after, and is able to heat the dermis/epidermis junction temperature to between about 45° C. and 55° C.

Yet further embodiment of the present invention envisions the energy source which comprises means for providing pulsed electromagnetic energy in the range of about 0.1 millisecond and about 1000 milliseconds, and providing lamp radiation before, during, after, and is able to heat the dermis/epidermis junction temperature so that combined with the energy deposited in the skin by pulse EM energy source, skin conditions are alleviated including the condition of acne.

Figure 15:
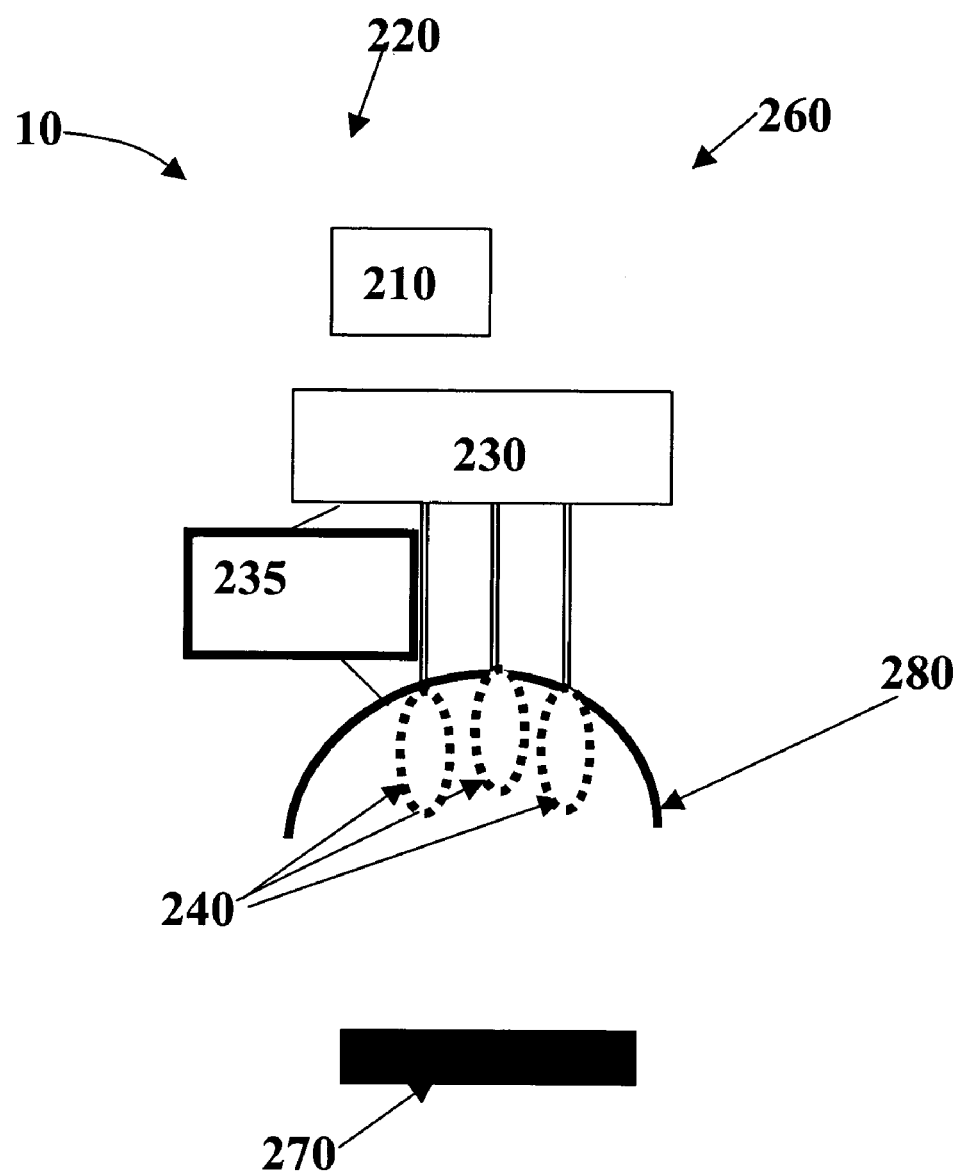
FIG. 15 is a sectional view showing the components of a light or electromagnetic radiation handheld acne treatment device with possible energy absorbing intermediate layer.

FIG. 15 shows an alternative embodiment of the handheld treatment device 200.

As shown in FIG. 15, the device has a power source 210 (a wall electric outlet, an electric transformer or a battery) that powers a circuit board 230. The circuit board 230 is activated with power switch 220 to charge a capacitor that stores enough energy to cause an electric discharge in the lamps 240. The circuit will then recharge the capacitor and be ready to fire again within a fraction of a second and up to a few seconds. In order to reduce the risk of accumulation of heat, the heating element having a high absorbing substance or other heating elements is allowed to cool down before another heating pulse is fired. In one embodiment, a temperature sensor (e.g. thermocouple) 250 may be use to monitor the temperature of the heating element and prevents a heating pulse until the temperature drops below a safe temperature (for example 35° Celsius or 40° Celsius). The capacitor is discharged when a fire button 260 is pushed.

In this embodiment of the present invention, flash lamps 240 are used to quickly heat a thin absorbing layer 270. A circuit board 230 can fire one or multiple lamps to control the total energy delivered to the thin absorbing layer 270. A reflector 280 collects the light that is radiated away and redirects it toward the absorbing layer 270 to uniformly heat the absorbing layer 270.

In this embodiment of the present invention, the high absorbing layer will be heated due to the optical energy it absorbs from the flash lamps and will then quickly transfer its energy to the skin through thermal conduction into tissue. The safety of the device is enhanced by the fact that the lamps are pulsed and they deposit a predetermined, known amount of energy into the high absorbing layer. The amount of energy transferred into the skin is, of course, always smaller then the amount of energy deposited in the optically absorbing layer.

As an example, for a 100 um thick absorbing insulator, such as a glass or plastic (capable of sustaining higher temperatures without melting) with similar thermal property, to be heated to 300° C., the energy deposited in such material layer which is initially at 30° C. is approximately 2.5 g/cc*100e-4 cm*(270 C)*0.84 J/g/C=5.7 J/cm². If we assume heating of the thin layer occurs within a short time compared to the thermal relaxation time, then the cooling time can be estimated from the thermal relaxation time. The relaxation time is approximately (100e-4/3.14)2/0.008=1.2 msec. For a 100 um thick copper layer heated to 300° C., the available energy to transfer to tissue that is at 30° C. is approximately 9.2 J/cm². The relaxation time is approximately 8.65 microseconds.

Additional embodiments of the present invention are described below:

A therapeutic treatment device comprises:

An incoherent electromagnetic energy source operable to provide a pulsed energy output from a plurality of energy sources having a spectrum of frequencies including a frequency bandwidth capable of being absorbed by an intermediate substance;

a housing with an opening, said light source being disposed in said housing, and said housing being suitable for being disposed adjacent to the intermediate substance;

a variable pulse-width pulse forming circuit electrically connected to said light source; a reflector mounted within said housing and proximate said light source, directing its energy towards said absorbing intermediate substance whose absorbing characteristics range from zero (completely transmitting) to infinity (completely absorbing).

In the device the incoherent energy source is supplemented with a laser energy directed at the general vicinity of the treatment area before, during or after the application of the pulsed energy output.

In the device substantially most of the energy of the electromagnetic energy source is deposited at the surface resulting in expansion of skin surface opening and discontinuities to allow at least some enhancement in the transport of material across the skin to alleviate skin conditions and ailment and to improve the look and condition of the skin.

The plurality of energy sources can be lamps with reflectors with electromagnetic energy output and wherein at least one lamp energy is intercepted by a high absorbing film mounted proximate to the lamp opening.

The energy source can be a flash lamp such as of the type used in digital and disposable (single use) cameras.

The energy source comprises means for providing pulses having a width in the range of between about 0.5 microseconds and 500 millisecond and an energy density of the light on the skin of more than about 0.1 J/cm² and less than about 2 J/cm².

The energy source comprises means for providing a pulse in the range of about 0.1 milliseconds to 2000 milliseconds, whereby skin opening may be expended to enhance transport across the skin.

The energy source comprises means for providing pulsed electromagnetic energy in the range of about 0.1 millisecond and about 1000 milliseconds, and providing laser CW light radiation before, during, or after said pulse radiation.

Said energy source comprises means for providing pulsed electromagnetic energy in the range of about 0.1 millisecond and about 1000 milliseconds, and providing laser CW light radiation before, during, or after said pulse radiation and providing lamp radiation before, during, after, and is able to heat the dermis/epidermis junction temperature to between about 45 degree C. and 55 degree C.

In the device said energy source comprises means for providing pulsed electromagnetic energy in the range of about 0.1 millisecond and about 1000 milliseconds, and providing lamp radiation before, during, after, and is able to heat the dermis/epidermis junction temperature to between about 45 degree C. and 55 degree C.

In the device said energy source comprises means for providing pulsed electromagnetic energy in the range of about 0.1 millisecond and about 1000 milliseconds, and providing lamp radiation before, during, after, and is able to heat the dermis/epidermis junction temperature so that combined with the energy deposited in the skin by pulse EM energy source, skin conditions are alleviated including the condition of acne.

In the device said light source comprises means for providing pulses having a width in the range of between substantially 0.05 microsecond and 1000 millisecond and an energy density of the light on the skin of less than about 10 J/cm$^2$.

In the device said light source comprises means for providing pulses having a width in the range of between substantially 0.1 millisec and 600 millisec and an energy density of the light on the skin of less than about 6 J/cm$^2$.

In the device said light source comprises means for providing plurality of pulses having a width in the range of between substantially 0.1 millisec and 600 millisec and an energy density of the light on the skin of more than 2.5 J/cm$^2$.

Figure 16:
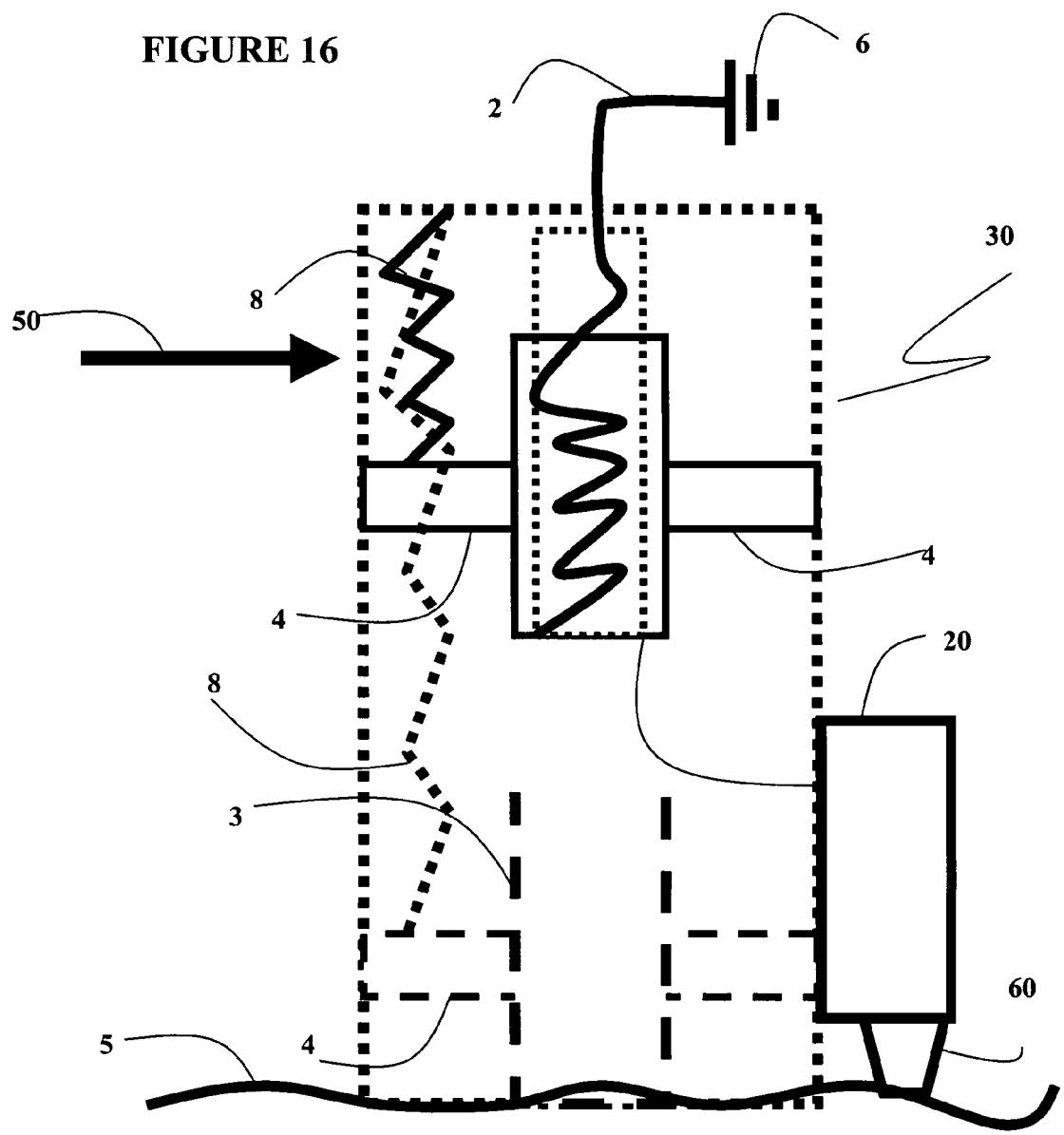
FIG. 16 is a sectional view showing the components of the handheld acne treatment device with a dispenser to allow the deliver of drug, nutrient or other elements to the skin.

As shown in FIG. 16, a console 1 contains a heat source 2 and a heat shuttle 3 which can be brought into contact with the heat source. The heat shuttle 3 has latches 4 which allow a motion promoter 8 (for example a spring) to push it towards the skin surface or other target surface 5, and then subsequently to discharge the excess heat energy, back towards the heat source 2. The heat source 2 (for example and electrical heater) contains an energy source 6 (for example, a battery or an electrical energy source, as shown), which generates the thermal energy within the heat source. Said thermal energy is subsequently delivered to the skin by means of the heat shuttle 3 or by forming contact with the target allowing thermal energy to diffuse directly into the skin.

FIG. 16 also shows the position of the heat shuttle 3 with respect to the target material surface 5 and the heat source 2 (for example, a winded wire resistor or some other type of thermal energy generating electrical resistor), when in contact with the skin. Note the extended form of the motion promoters 8.

As is also shown in FIG. 16, the device can also be envisioned to work in combination with a dispenser of a drug or nutrient or any other substance that one desires to deliver into the surface and in particular into the skin. A container 20 carrying the desired substances can be attached to the device 30 and as the device is moved as shown by the direction of the arrow 50. The container 20 dispenses its substance through a dispenser 60 which can be brought into contact with the target surface and in particular with the target skin. If the dispenser assembly 20 and 60 precedes the action of the HS device 30 as when the motion is in the direction of the arrow 50, then the HS device 30 acts on the material to drive it into the target surface or skin. However, if the dispenser assembly 20 and 60 follows the action of the HS device 30 as when the motion is in the direction of the arrow 40, then the HS device 30 acts on the target material or skin to modify said target surface or skin and enhance the material that is delivered subsequent to the HS device 30 action.

In another preferred embodiment, laser source (preferably a diode with continuous wave (CW) emission power of about 0.5 W to about 10 W and preferably with a CW emission power of about 1 W to about 2 W) is focused to a line (e.g. ~1 cm long) with a cylindrical lens.

The device comprises:
a trigger that releases a hook,
a hook that holds a mirror that is spring loaded,
a spring that forces the mirror to move thus moving the line,
a scanned line that makes a rectangle scan of about 1 cm×1 cm in area,
a small electric motor then reloads the spring/mirror to its original position and the hook latches back on.

The trigger also releases two other safety shutters:
1. One is connected to the electrical motor and is designed to flip open/shut a bit slower than the time it take the mirror to do its scan.

2. The second is mechanical and can either be designed to close automatically (e.g., a spring loaded one and its hook is designed to release a spring that closes it e.g. 10 ms after the scan begins.

Or it can be designed to remain open as long as the finger is on the trigger. The light scans an area that is larger than the opening of the device. The opening of the device is design to allow only the approximately linear and constant velocity of the scanned light through, i.e., the acceleration/deceleration portions are cut out of the opening and do not make it out of the device.

The light scans the surface of a HAS film which we call a "bullet".

The bullet comes out of a magazine loaded with e.g. about 30 bullets. 30 Bullets should be enough to cover an entire face.

The bullets in the magazine are spring loaded and come out with each device trigger action.

Each trigger action also removes the old bullet (e.g. the new bullet pushes the old out) into a disposable collector.

Each bullet may be soaked with a lotion for Anti aging or wrinkle treatment, Oil of Oley, acne ointment, nutrients vitamins or any other substance that one may wish to deliver trans-dermally.

Alternatively, a reservoir of said desired fluids or creams to be delivered trans-dermally into the skin or any other target surface may dispense the desired material either before, during or after the light scanning action.

Figure 17:
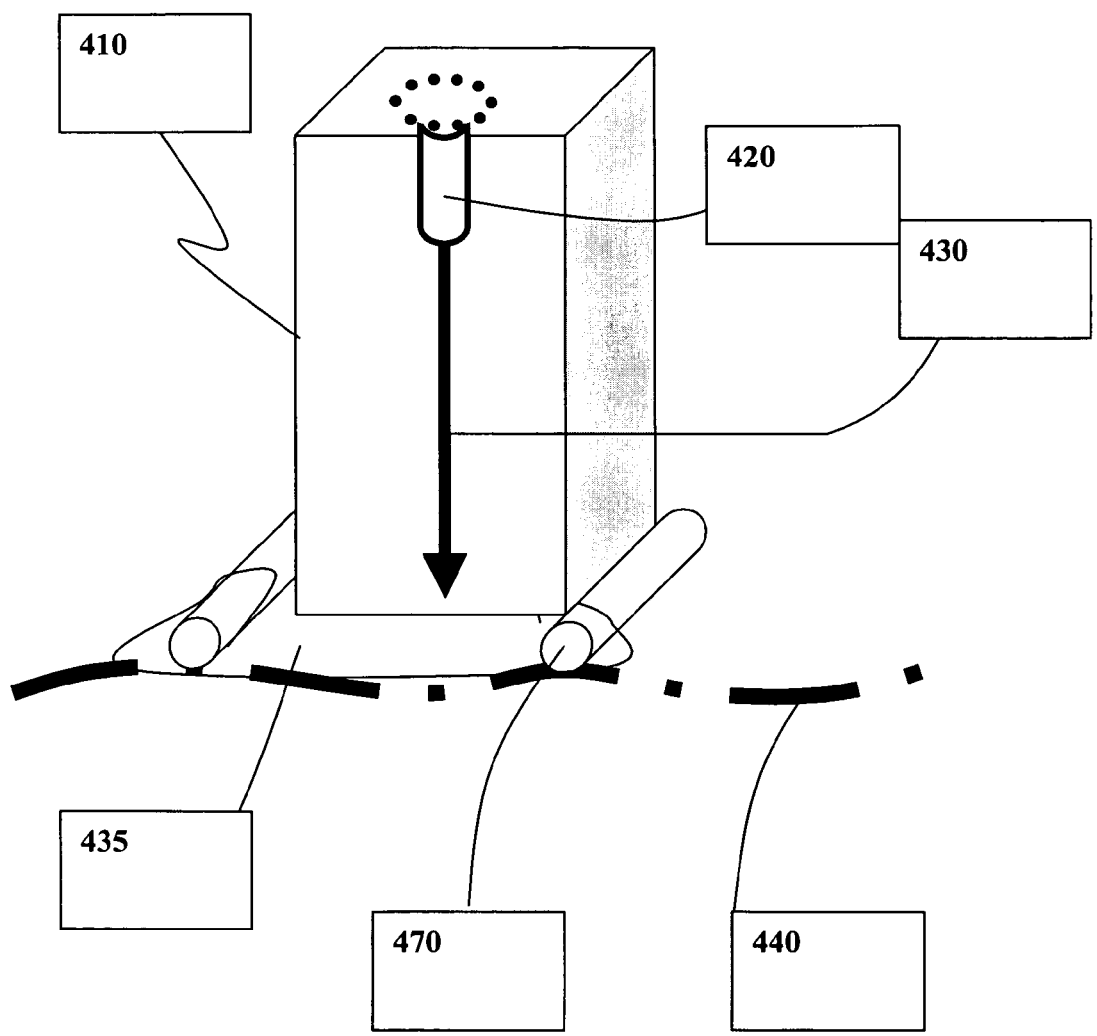
FIG. 17 is a sectional view showing the components of the enclosures of a possible embodiment of a skin treatment device utilizing a light source and a high absorbing substance being rolled up and replenished by the motion of two rollers.

FIG. 17 illustrates yet another preferred embodiment of the present invention. In this embodiment, the energy source 420 contained within the encasing 410 is a broadband emitter of energy. In yet another preferred embodiment, the energy source is a source of electromagnetic radiation and preferably a broadband electromagnetic radiation with a spectral range from about 350 nm to about 2000 nm and preferably from about 400 nm to about 1100 nm.

In a modification to this embodiment, the energy source 420 is a flash lamp, preferably a flash lamp with approximately the same characteristics as those of most disposable one-time use camera on the US market. In this embodiment, such energy sources are light source with small flash lamp capable of illuminating a field of up to 20 feet and are powered by a 1.5-volt battery or two 1.5 volt batteries and at least one capacitor and the electronic circuitry to discharge and recharge it.

In a preferred embodiment, a high absorbing substance (HAS) film 435 or a partially transmitting HAS film 435, which is mounted on rollers 470, is used to convert at least some of the flash lamp's energy into thermal energy. The film is in contact with the targeted surface or skin and thus is capable of transferring said converted optical energy from the flesh lamp to the film and to the target surface or skin so that a beneficial change to the skin condition or the target surface does occur.

In yet another preferred embodiment said targeted HAS film is made of disposable material either on roller or on removable disposable caps so that it is replaced from energy discharge to the next or from use to use or from time to time. In another preferred embodiment, the flash energy source or the entire assembly is a single use or made to be used only for a few firing of the energy source and then being replaced from time to time. Here, the light from the energy source 420 (preferably a laser) impinges on the a film (407) saturated with a substance of high absorbance in at least one spectral band of energy radiation 330 coming out of the energy source 420. The energy beam 420 then interacts with the film and its energy is converted into thermal energy that subsequently propagates into the targeted surface or skin 440. A set of rollers 470 dispenses the disposable containing high absorbing substance film and collects it on the other side.

Alternatively, the film 440 can be made of a pattern of absorber regions and transmitting regions wherein the absorbers can be made, for example, in a preferred pattern, a pattern of absorbing dot matrix or absorbing lines and the rest of the film is made of transmitting material.

Figure 18:
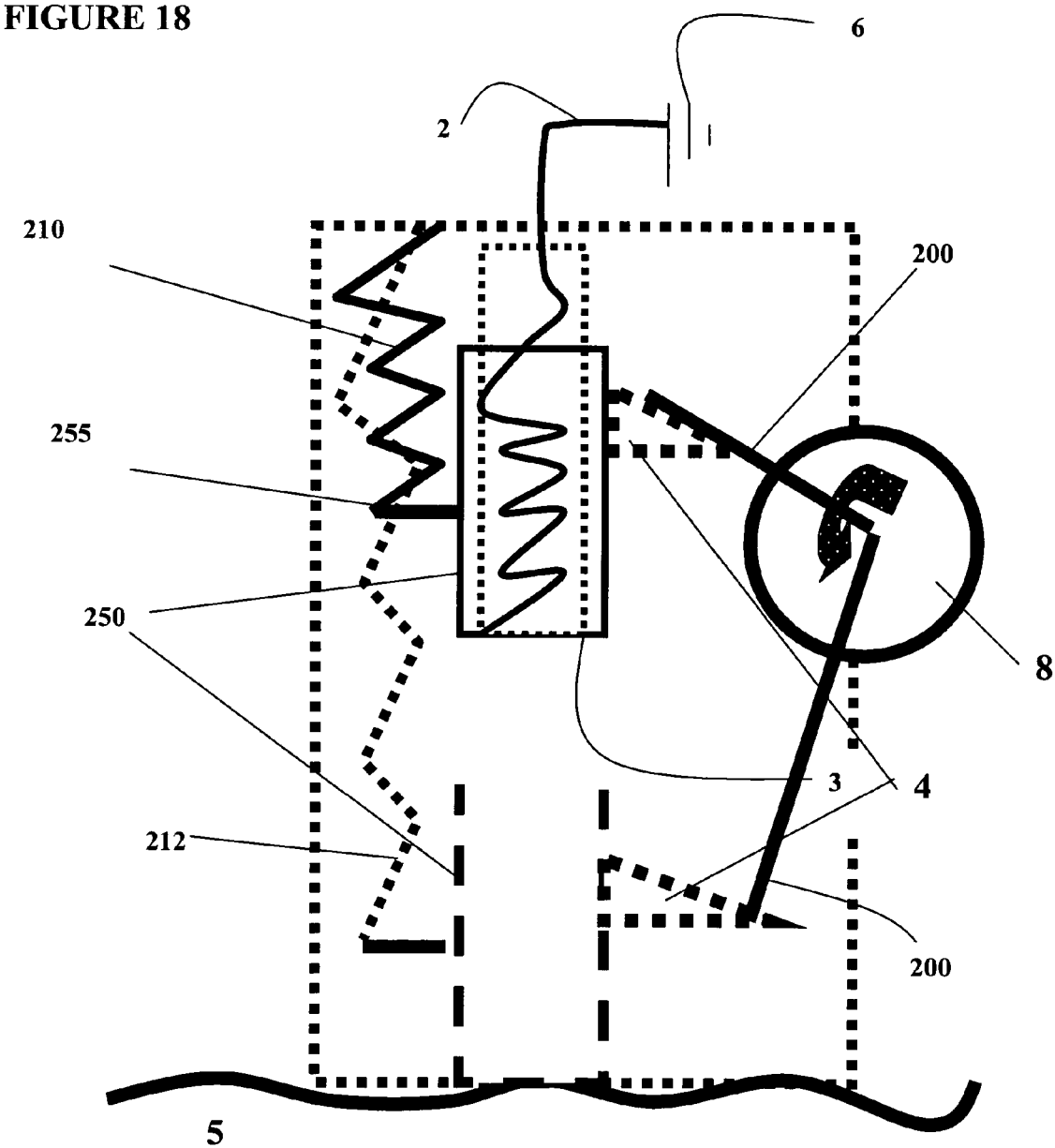
FIG. 18 is a sectional view showing the components of an electrical heating delivering its energy to the skin through the intermediate use of a movable heat carrier.

FIG. 18 describes another preferred embodiment of the present invention. Here the device 30 is modified so that the motion promoter element 8 of the heat shuttle is a motor, preferably an electrical motor. As the motor turns, it pushes with its bar 200 on the latches 4 which in this case is in the shape of a wedge as shown. As the motor spins, the latch 4 along with the heat shuttle is pushed downward. The latches 4 and the bar are designed to be in contact so that the motor pushes all the way to the skin or target surface 5. When contact is made, the bar 200 continues to push again the latches down so that the heat shuttle is forced into a good contact with the skin. The bar 200 at that time is just about clearing its contact with the latches 4. The latches 4 are made of somewhat flexible material (e.g. like a hard rubber rod) and as the motor 8 continues to push the bar 200 again the rubber latches 4, the bar slips off the latches wedge and the latches are no longer pushed by the motor 8 and its bar 200. The heat shuttle is spring loaded with a spring 210 as shown, and is thus pulled back all the way up and back into contact with the heating element 2. Position 212 shows the spring in its extended position.

Figure 19:
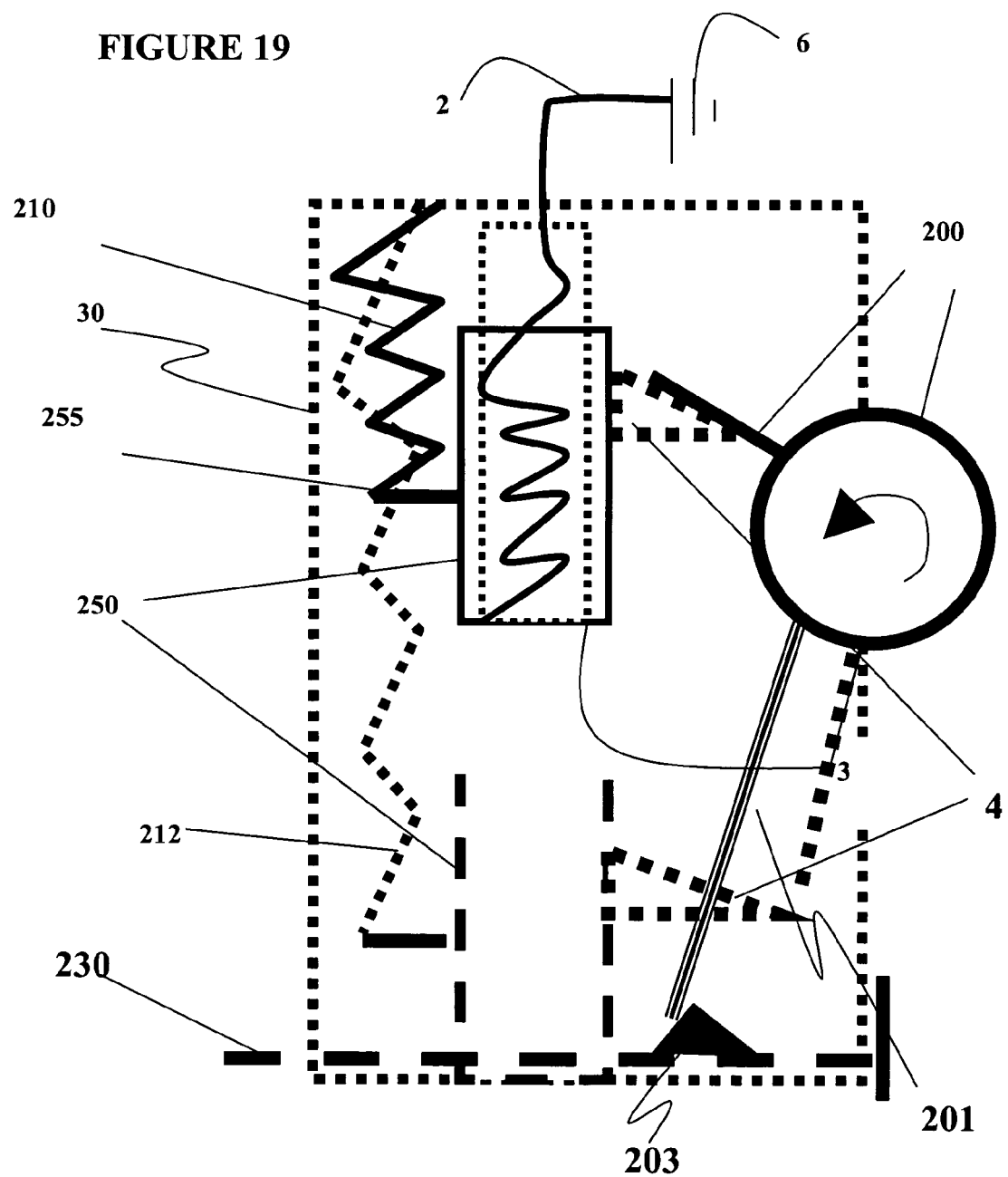
FIG. 19 is a sectional view showing the components of an electrical heating delivering its energy to the skin through the intermediate use of a movable heat carrier further comprising the use of a shutter.

Alternatively, in another preferred embodiment shown in FIG. 19, the motor also actuates in a simultaneous motion a a second bar 201 that pushes against another wedge 203 that is connected to a shutter 230 causing it to open as the heat shuttle descend. With the same mechanism utilizing the motor 8 rotational motion and the wedge 203, at some point, the wedge 203 is released and spring 240 pushes the shutter back to cover the target the surface. Wedge 203 can also have other shapes such as a bar or a projection. The complete clearing of the device 30 opening by the shutter is designed to happen just before the HS is about to make contact with the target surface or skin. As the shutter is pushed back by the spring 240 it may be utilized to push out the bottom portion of the HS 250 which is thus made to be a disposable part utilized only once in each contact. (i.e. a disposable "bullet" in the description above).

Figure 20:
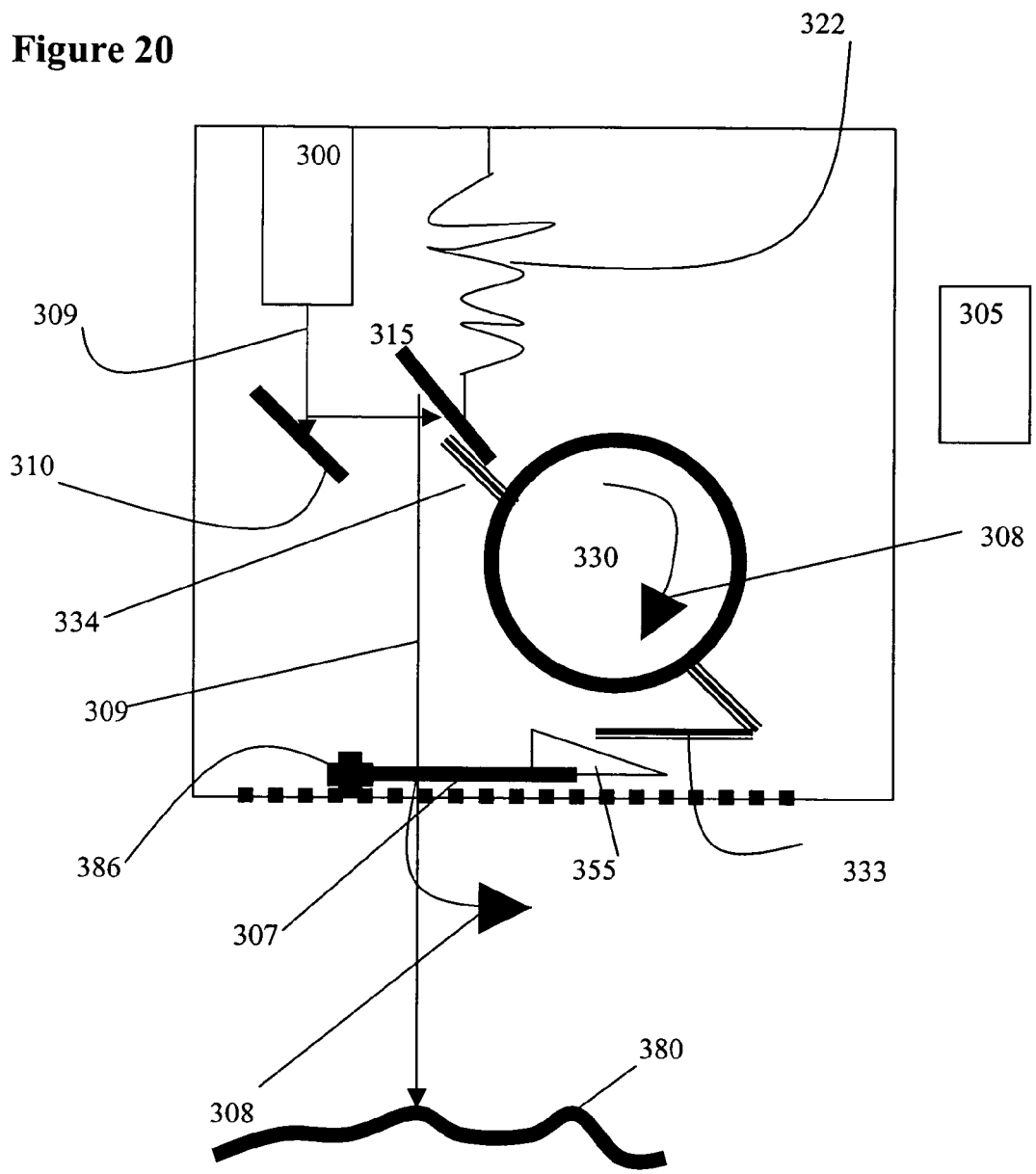
FIG. 20 is a sectional view showing the component of a light based handheld acne treatment device utilizing motor-driven mirror scanning and shutter operation.

As shown in FIG. 20, another preferred embodiment of the present invention utilizes the dual push mechanism described by FIG. 20 to generate a mechanical scan synchronized with the action of a shutter to ensure safety and automated shut off.

A continuous wave laser 300 is activated when an on/off trigger 305 is pushed. The on/off trigger also opens a master shutter 307. The on/off switch also trigger the rotation of a motor 330. Two bars 333 and 334 which are attached to the motor move the mirror 315 and the hedge attached to the shutter 307. The spring 322 is compressed during the motorized wheel motion to move the mirror and once the bar 334 releases the mirror 315, the spring 322 pushes it back to its original position.

The beam from the laser 300 bounces off the mirror 310 to the swinging/scanning mirror 315 and then out through the opening when the shutter 307 is swung open. In this embodiment an exemplary operation of the device sown in FIG. 20 utilizes a bar 334, bar 334 is pushed against the scanning mirror 315 which is then moved (in this case upward) at the desired rate. When the bar 334 slips off the mirror (the mirror edge can be shaped as a wedge to facilitate such slippage) the mirror 315 is pushed back rapidly by a spring 322 that returns it to its original position. The rotational motion of the motor 330 provides a uniform scan rate for the mirror.

Simultaneously to this motion, the other bar 333, which is attached to the motor 330, is pushed against the wedge 355 to cause a second shutter 307 to be open (in the direction of the arrow 308) at a uniform rate. As the shutter 307 swings open it allows the scanning laser beam 309 to be moved synchronously with the motion of the scanning mirror to allow the beam through the shutter 307 and into interaction with the target surface or skin 380. When the bar 333 slips off the ledge 355 the shutter 307 is rapidly pushed back by spring loading component 386 forcing the shutter 307 to its close shut, thus preventing the beam from reaching the target surface or skin 380.

Figure 21:
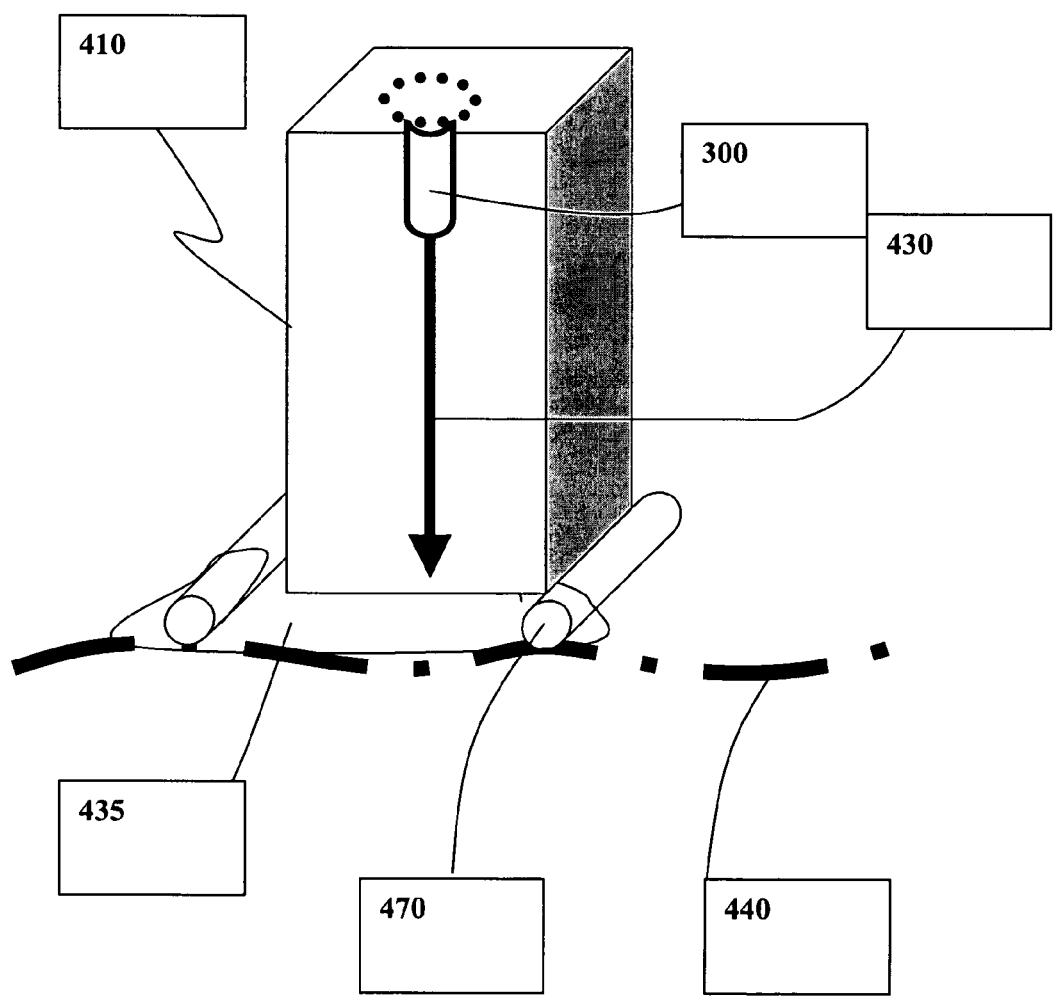
FIG. 21 is a sectional view showing the components of the enclosures of a possible embodiment of a skin treatment device utilizing a light source and a high absorbing substance of various pattern and various degrees of transmission being rolled up and replenished by the motion of two rollers.

As shown in FIG. 21, yet another preferred embodiment of the present invention pertains to opto-thermal interaction with a target surface or a skin as shown in FIG. 21. Here, the light from the energy source 300 (preferably a laser) impinges on a film 435 saturated with a substance of high absorbance in at least one spectral band of energy radiation 430 coming out of the energy source 300. The energy beam 430 then interacts with the film and its energy is converted into thermal energy that subsequently propagates into the targeted surface or skin 440. A set of rollers 470 dispenses a disposable film containing high absorbing substance film and collects it on the other side.

Alternatively, the film 435 can be made of a pattern of absorber regions and transmitting regions wherein the absorbers can be made, for example, in a preferred pattern, a pattern of absorbing dot matrix or absorbing lines and the rest of the film is made of transmitting material.

Figure 22:
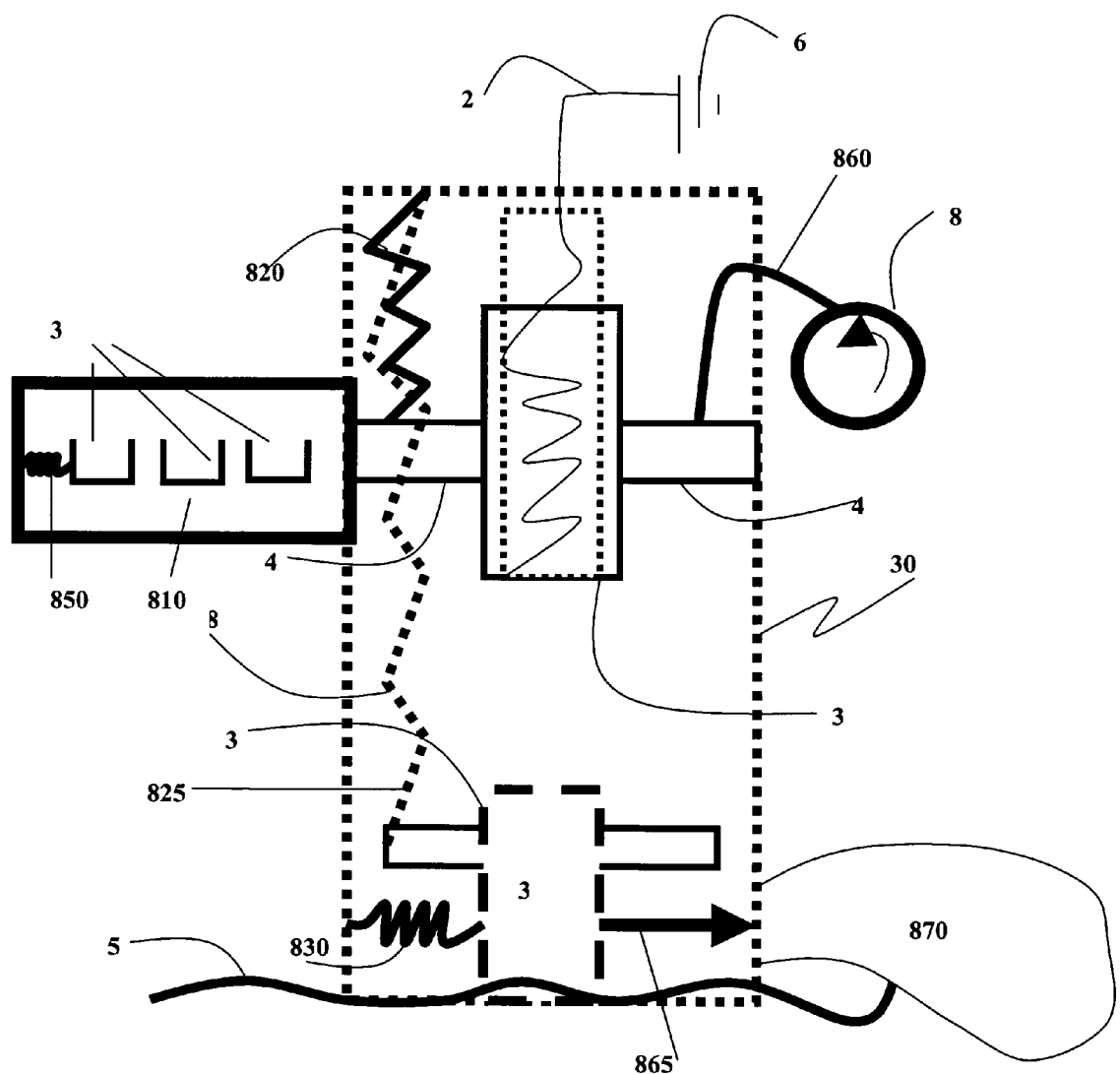
FIG. 22 is a sectional view showing the component of an electric heating transport heat shuttle with disposable shuttle units.

FIG. 22 illustrates a device 30 for electro thermal surface treatment (including skin conditions such as acne) wherein the heat shuttle 3 is now a disposable element that is stored in a magazine (or clip) 810 full of additional disposable heat shuttles 3 (like "bullets" stored in a clip).

A spring 850 propels the "bullets" heat shuttles 3 towards the heating element energy source 2 where the bullets 3 are secured and kept in contact with the heat source through the force provided by a spring 820. A motion propeller 8 which can be an electric motor 8 pushes on the latch 4, and move the heat shuttle away from the heat source and into contact with the target surface or skin 5.

Once in contact with the target surface or skin 5, the motion promoter (e.g. an electric motor) arm 860 slips off the heat shuttle handle bar 4 and no longer forces a pressure of the heat shuttle 3 on the target surface or skin 5. At that time, a removing mechanism consisting of a spring 830 is released and pushes the used heat shuttle 3 away from the skin as shown by the arrow 865 and into a disposed heat shuttle collecting pouch 870.

Figure 23:
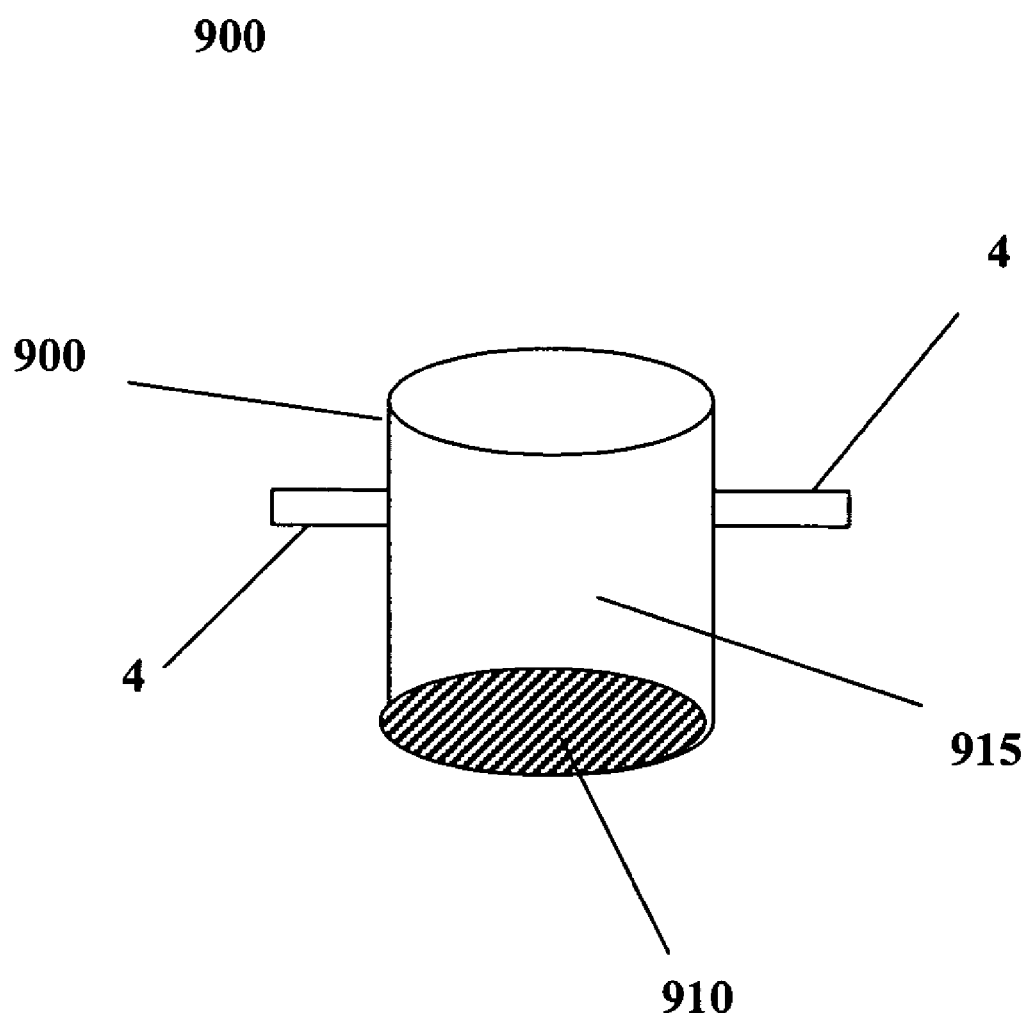
FIG. 23 is a sectional view showing possible components of a heat transporter heat shuttle.

FIG. 23 illustrates an exemplary composition and construction of a disposable heat shuttle 900 as used in the preferred embodiment of FIG. 22. The body of the heat shuttle 900 is made to fit around the heat source. The body 915 of the shuttle can be made for example from an insulating material, for example, a plastic, glass, or Teflon that are capable of withstanding high temperature (for example up to about 400 to 500 degree C.) without deformation or chemical changes to them. The body 915 can also be made of metal (for example, copper, or aluminum) to allow heating of the body 915 itself and not just the active element 910 at the bottom. There is at least one bar or latch 4, which is used to push the heat shuttle 900 against the heat source. At the bottom of the heat shuttle 900 there is an active element 910 for thermal energy storage and capable of contacting both the heat source for the purpose of uploading thermal energy and, subsequently, for contacting the target surface or skin, for the purpose of conducting its thermal energy to the target surface or skin and unloading its thermal energy to the target surface or skin. The active element 910 can be any material capable of being heated by a hot body such as an electrical heater or an soldering iron. The active element 910, however, must be capable of easily conducting its thermal energy into the target skin. Therefore the active element 910 is preferably made of metal such as copper, or aluminum.

Figure 24:
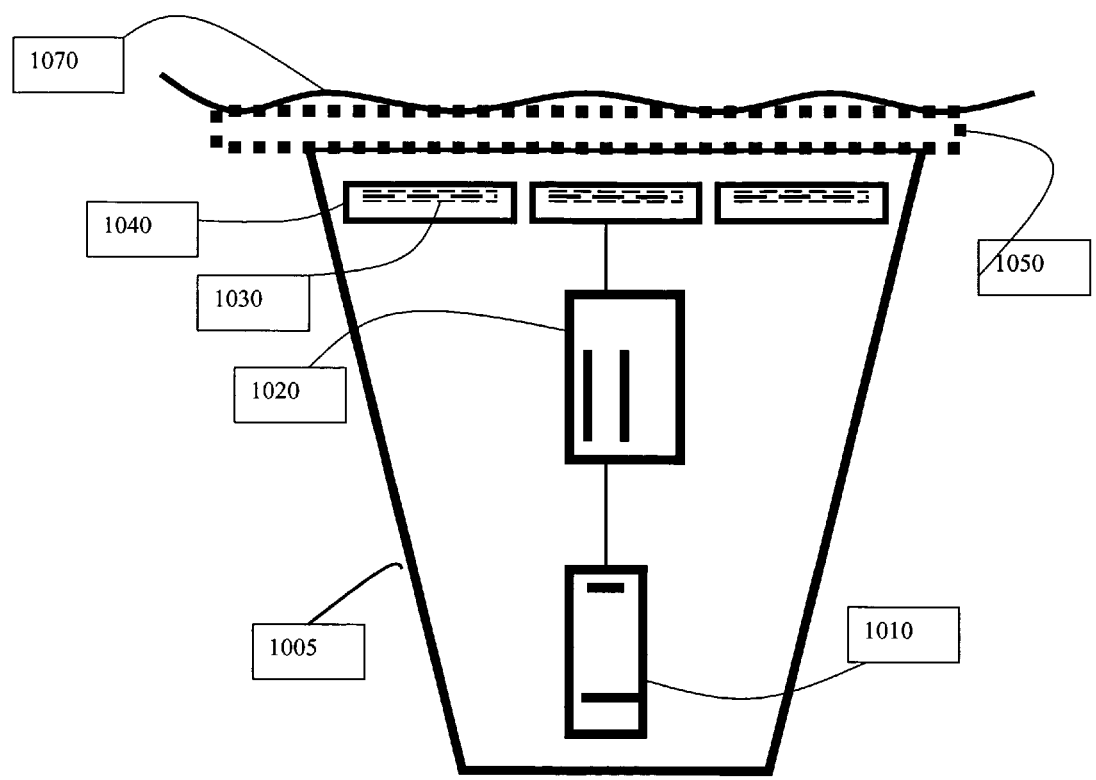
FIG. 24 is a sectional view showing possible components of an optical light or flash lamps handheld acne treatment device.

FIG. 24 shows yet another preferred embodiment. Here, a housing 1005 contains the entire apparatus. An energy source 1010, (for example, can be a 1.5V AA battery or two of them) charges a capacitor 1020. The capacitor discharge allows a flash lamp (or other component capable of generating electromagnetic energy) 1030 to emit electromagnetic energy of known amount in known time duration (these can be easily calculated by a person skilled in the art). The generator of electromagnetic energy or flash lamp is positioned inside a lamp housing 1040. A thermo-optical converter 1050 then absorbs the electromagnetic energy and converts it into heat. The thermo-optical converter 1050 can be brought close to or in contact with the skin 1070 and transmits the thermal energy to the skin. In an alternative preferred embodiment, the thermo-optical converter 1050 is composed of some portion that are fully transmitting of the electromagnetic energy, some portion are partially transmitting and partially absorbing the electromagnetic energy, and some portions of the thermo-optical converter are fully absorbing of said electromagnetic energy or flash lamp energy. The amounts of energy that are fully absorbed, fully transmitted, and partially transmitted and their location on the thermo-optical converter 1050 surface, can be varied according to the desired effect and how much energy is desired at each surface location versus how much energy the user wish to allow to penetrate the surface and heat the surface below.

In another preferred embodiment, multiple flash lamps or electromagnetic energy generators 1030 (and their related energy sources 1010, and capacitors 1020) are packed into a single housing 1005 to allow the user larger area coverage or to increase total energy delivery into a desired treatment area. In another preferred embodiment, said multiple flash lamps or electromagnetic energy generators 1030 are willfully triggered in a desired sequence and multiple times to create a repeated illumination of the same electro thermal converter surface area or a pattern of sequential illumination of different regions within the opto-thermal converter area or a combination of the two.

The present invention proposes and utilizes the concept of thermal energy application to modify the skin or target surface condition to allow modification of the surface for treatment of hair follicles conditions and sebaceous gland conditions. The idea is based on the relative expansion and forced separation of adjacent points on an elastic surface. Just like an expanding balloon, where the relative distance with the expansion of the universe, so do the boundaries of the pores and indeed every point on the expanding skin. Each point on the surface of the balloon is separating and increasing its distance from its neighbor. If one draws a hair follicle opening on such a surface it is clear that said hair follicles opening boundaries are increasing in size with said expansion. Since different material increase at different spatial rate with increase temperature (and increase thermal energy) the result is a disruption in the bond of a plug in the pore opening of the hair follicles and the pore walls occurs. Such result allows dislodging of the plug and enhanced drainage of the unwanted material from inside the surface of the target material or the skin to the outside.

In another preferred embodiment, one may add a substance with high coefficient of thermal expansion to the opening of the pore. One may also try to force such a substance of high thermal expansion coefficient into the target surface opening or skin pores. Such a substance may increase and enhance the relative displacement of the pore opening walls with respect to the plugging material and debris that cause the plugging.

The present invention is based, at least in part, on the discovery that energy can modify skin structure in a reversible way so as to mitigate sebaceous gland caused conditions as well as cure sebaceous gland disorders, e.g., eliminate, inhibit, or prevent occurrence or reoccurrence of the skin disorder. A preferred example of such a sebaceous gland disorder is acne.

Since many undesirable skin conditions result from the blockage of the skin pores, a method for changing the skin pore size and ability to transport fluid was developed using thermal energy. Thermal energy causes material to expand. The exact extent, manner, and amount of expansion are dependent on the parameters of the energy application process. In addition, the extent of the collateral effect (e.g. collateral damage or nature of changes to the skin tissue or target material) is also dependent on parameters of energy application.

In its most general form, continuous application of large amount of energy will cause expansion of the skin or target material but said applied energy will also diffuse into the tissue and may cause unwanted damage to the dermis or deeper lying structure of the target material. In one preferred embodiment of the current invention, thermal energy is applied substantially to the surface of the material or skin in quanta. It can also be brought about via the use energy quanta loaded onto a shuttle that carries that energy from a heat source to the target material or skin If said energy quanta is unloaded in a rapid manner, (as would be the case for example, when a heated metal body contact the surface of the skin) its excess energy would rapidly flow into the surface of the material and substantially remain their for a duration which is dependent on the thermal conductive nature of the skin or target material. This action creates a pulsed heating of the skin and has the additional advantage of predetermining the total amount of energy delivered to the skin.

With knowledge of the thermal conductivity of the skin, one can calculate what is the amount of energy that is launched into a predetermined volume and the time-dependent characteristics of such a heating process. In one embodiment of the present invention, we contemplate heating of the upper volume of the skin (for example, from about 5 um depth and down to about 300 um from the surface of the skin,) to a temperature of from about 30 degree centigrade and up to about 400 degrees centigrade for duration of up to about 100 ms. Such a heating range will cause sufficient thermal expansion to allow material to enhanced material flow in and out of the skin pores.

The process can then be repeated by removing the energy transporter form the skin and either reloading it with energy to be delivered to the skin or target material or loading a new transporting element with energy and repeating the process.

Depending on the desired effect, the process can be repeated either in such a way that allow dissipation of the energy that was deposited in the skin by the preceding energy transporter, (i.e. so that the temperature of the skin return to its normal level and all excess energy has been dissipated) or in such a way as to built up in cumulative energy deposition so that beyond the spikes in energy build up there is also average temperature increase in of the upper layers of the skin.

Such cumulative energy built up the associated temperature increase can be useful in, for example, enhancing circulation, stimulating collagen build up, stimulating healing, enhancing activity and penetrating of drugs and substance that have beneficial effects if delivered into the skin, enhancing removal of substances that has bad influences or negative effect on the health or well being of the skin. Such material and sebum removal can be aided by a preceding, simultaneous or following actions of vacuum pumps and suction devices. Such deposition can be aided by a preceding, simultaneous or subsequent substance delivery action such as ultrasound, electropherosis or any other devices or methods that allow substance to be driven or pushed into the skin.

The energy quanta delivery process has the additional advantage of predetermining the collateral effects and collateral damage of the process or the device. This is the case because if no excess energy is loaded into said energy shuttle no excess damage can occur. The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is based, at least in part, on the discovery that thermal energy action can be used to treat sebaceous gland disorders, e.g., eliminate, remove, or prevent occurrence or reoccurrence of the sebaceous gland disorder. Examples of such sebaceous gland disorders include sebaceous gland hyperplasia, acne vulgaris and acne rosacea. A preferred example of such a sebaceous gland disorder is acne.

The present invention also pertains to methods for modifying the opening to the infundibulum by applying thermal energy to the opening to the infundibulum. A sufficient amount of the energy is deposited at the surface of the skin to causes an expansion of the region of the infundibulum, thereby modifying the opening to the infundibulum. In one embodiment, the opening to the infundibulum is altered such that pore pluggage will not occur, e.g., the infundibulum shape is modified temporarily or permanently such that excess sebum, oils, dirt and bacteria will not cause pore pluggage to occur, resulting in a blackhead (comedon) or white head (milium). In a preferred embodiment, the opening to the infundibulum is opened.

Sebaceous glands are components of the pilosebaceous unit. They are located throughout the body, especially on the face and upper trunk, and produce sebum, a lipid-rich secretion that coats the hair and the epidermal surface. Sebaceous glands are involved in the pathogenesis of several diseases, the most frequent one being acne vulgaris. Acne is a disease characterized by the occlusion of follicles by plugs made out of abnormally shed keratinocytes of the infundibulum (upper portion of the hair follicle) in the setting of excess sebum production by hyperactive sebaceous glands. Various treatment modalities for acne exist that aim in modifying the rate of sebum secretion by the sebaceous glands (e.g., retinoids), inhibiting the bacterial overgrowth in the follicular duct (antibiotics), or decreasing the inflammation of acne lesions (anti-inflammatory agents). Most of these agents are not curative of acne and simply control the disease by affecting one of the aforementioned pathogenic factors. Oral retinoids are a notable exception: they are potent drugs that can achieve a significant cure rate for acne, but their side effect profile often limits their use. Advantages of the present invention include that treatment can permanently or temporarily (and reversibly) alter the pilosebaceous unit, rendering it no longer susceptible to pore pluggage but without the side effects associated with oral retinoids.

The term "sebaceous gland disorders" is intended to include those sebaceous gland disorders which can be treated by the delivery of thermal energy.

Thermal energy quanta can interact with the site of pore pluggage, inflammation, bacteria, viruses, etc. and promote, for example. Examples of sebaceous gland disorders which can be treated by the methods of the invention include sebaceous gland hyperplasia, acne vulgaris and acne rosacea. Of particular importance is treatment of acne by the method of the invention.

The term "pluggage" is intended to obstruction of the pores by the buildup of sebum, dirt, bacteria, mites, oils, and/or cosmetics in the pore, e.g., about the infundibulum. The term "acne" is recognized but those skilled in the art and is intended to include acne vulgaris and acne rosacea. Acne vulgaris the most common skin disease seen in dermatologic practice which affects approximately 17 million people in the United States. Its precise cause is unknown, although abnormal keratin production with obstruction of the follicular opening, increased production of sebum (lipids secreted by the androgen-sensitive sebaceous glands), proliferation of Propionibacterium acnes (anaerobic follicular diphtheroids), follicular rupture and follicular mites (demodex) are commonly associated with acne.

Skin conditions such as acne are believed to be caused or exacerbated by excessive sebum flow produced by sebaceous glands most of which are adjacent to and discharge sebum into, hair follicles. Sebum is composed of keratin, fat, wax and cellular debris. Sebum forms a moist, oily, acidic film that is mildly antibacterial and antifungal and may to some extent protect the skin against drying. It is known that the bacteria which contribute to acne, Propionibacterium acnes or (P-acnes), grows in sebum. Significant sebum flow in humans begins at puberty. This is when acne problems generally arise.

The term "thermal interactions" (therapeutic, conditioning, or simulative) is recognized by those skilled in the art and is intended to include interactions, which are due to conversion of energy into various form of thermal energy or heat. For example, incident electromagnetic energy or light impinging upon a substance capable of absorbing such energy causes the absorbing substance to be energized and the material becomes heated. Further transmission of the energy to the target material via conduction, convection, or radioactive transfer result in the heating of the target area, preferably selectively with a significant temperature increase of such that unwanted material, e.g., tissues, oils, bacteria, viruses, dirt, etc. are removed. Preferably, the target heating is such that the surrounding tissue remains unaffected. The photothermally or thermally targeted material can also form biologically reactive products that further inhibits skin disorder or modify and condition the target material. Such thermal activation processes can involve oxidation of, for example, cell walls, extra-cellular matrix components, nuclei, etc. As a result of thermal action, the infundibulum can be temporarily or permanently reshaped. Additionally, the process can cause cell death in the sebaceous gland, thereby decreasing production of sebum.

Thermal alteration of the follicle infundibulum requires the deposition of sufficient energy to cause local heating to temperatures capable to bring about sufficient volumetric changes in the tissue. In general, these temperatures range from about 30 degree C. to about 500 degree C. for a range of expansion of the pore opening and preferably from about 50 degree C. to about 350 degree C.

The time duration of the thermal energy deposition which is sufficient to cause thermally induced changes in the blocked region of the follicular opening, can be determined by considering the basic principles of thermal diffusion. If the thermal energy is delivered within the thermal relaxation time for the target structure, heat flow from the target volume is limited during the thermal delivery time. The preferred thermal delivery time is therefore about equal to or less than the thermal relaxation time of the given target, which measured in seconds is approximately equal to the square of the target's shortest dimension measured in millimeters.

In most skin disorder treatments that involve minimizing the effect to the non-vascular part of the skin (layers without blood vessels or capillary) the interaction should be confined to the epidermis. If we take the epidermal thickness to be on the order of about 100 micrometer, the thermal diffusion time is on the order of about 10 millisecond. The thermal energy delivery phase to the skin should thus be confined to less than about 10 millisecond. As another example, the infundibulum portion of most sebaceous follicles on the face is approximately 0.3 mm in diameter and the relevant depth is also on the range of about 0.1 mm to about 0.4 mm and preferably about 0.2.mm This corresponds approximately to a thermal relaxation time of from about 0.01 seconds to about 0.1 seconds (100 ms). In practice, the present invention contemplates thermal diffusion into the relevant tissue depth in time duration sufficient to achieve thermo-mechanical expansion of the skin within the heated volume. The present invention does not contemplate collagen shrinkage as mean for achieving changes in the follicular opening to the skin as in the Anderson patent.

Although thermal confinement can achieved with laser pulse energy, for example pulses shorter than the target's thermal relaxation time, very short pulses cause unwanted mechanical injury, which can rupture the follicles. The fatty acids, sebum, and bacteria present in sebaceous follicles are extremely irritating if not contained by the follicle. In acne vulgaris, rupture of the follicle is an event, which stimulates inflammation to form a "pimple", including accumulation of pus to form a "whitehead". It is therefore desired to avoid rupture of the follicle or sebaceous gland.

The present invention offers a method for avoiding such mechanical injury by allowing the surface of the skin to expand like a membrane or a balloon surface. A weak location at or near the skin surface in the infected area or pimple is the connection of the plug material to the wall of the follicle which. Thus, when the targeted surface is forced to expand, the expansion allows separation of the plug boundaries from the walls of the follicle opening and at least some opening between the follicle walls and the plugging material. This, in turn allows drainage of the infected interior. The expansion of the follicle opening may allow excess sebum, oils, dirt and bacteria to be expelled so that pore pluggage will not occur, avoiding such conditions as black heads (comedon) or white heads (milium). Alternatively, a material capable of enhanced absorption of energy may be selectively deposited only at the follicular opening and be caused, after being activated through contact with hot (thermal energy loaded) material, to expand and thermo mechanically push the walls of the opening of the follicle allowing them to expand. Such thermal energy activated material that expand as a result of contact with the hot item can be, for example, animal fat or any other material that has larger volume expansion coefficient than the skin (or any target surface) itself.

The calculation for a simple model of target material water-based volume expansion and temperature increase is illustrated below.

1) Energy needed to increase the temperature of a given volume (Volume=Area*Depth) to a temperature DT is:

$$C=DE/DT \grave{o} DE=CDT$$

$$DE=C\,DT=c*Ro*\text{Volume}*DT$$

$$DE=c\,Ro\,A*\text{Depth}*DT$$

Specific heat capacity water–4.187 kJ/kgK=C
Hence $$DE=DT \times 4.2\ \text{KJ}/(\text{KG}*\text{K})$$

Volume=10 um×Cm$^2$=1E-5×1E-4 m$^3$
Volume=1E-9 m$^3$
Density=Kg/m$^3$
Mass=M=1E-9 Kg
=1E-6 Gram=ug
With DT=100 C $$DE=4.18\ (\text{kJ/Kg})\ 1\text{E-}9\ \text{Kg/K}*100\ \text{K}=4.2\ \text{E-}7\ \text{KJ}$$

Hence $$DE=4.2\ 1\text{E-}7\ \text{KJ} \sim 4\ \text{E-}4\text{J}=0.4\ \text{mJ}$$

Figure 25:
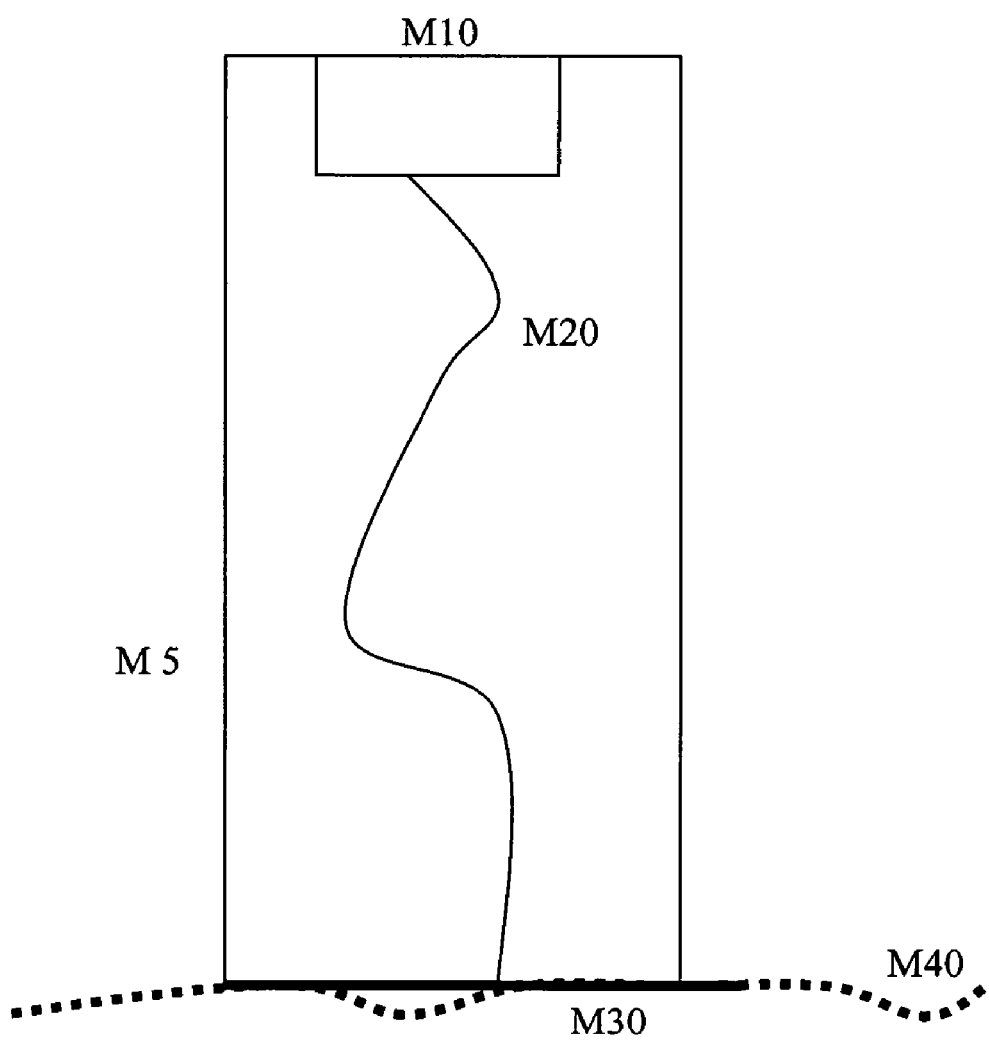
FIG. 25 is a sectional view showing possible components of an electrical heat handheld acne treatment device.

Para (DT, Depth=dZ) In water
The area considered in this example is generally about 1 cm$^2$.
DE=the energy needed to raise and area of 1 cm$^2$ and of a depth=dZ, To Temperature DT (mJ).
Finally additional preferred embodiments are described below:

FIG. 25: The present invention contemplates a method for treating skin conditions including acne by means of generating heat at the surface of the skin so that skin conditions are alleviated or improved.

In one preferred embodiment an energy source M10 is caused to willfully generate energy that is conducted by intermediate media M20 to a treating head M30 which is in contact with the skin. Such energy source can be made, for example from an electrical energy source such as a battery or an electric power supply or an electric plug. A conducting intermediate media can be made for example from electric wires and the treating head can be made, for example from an electric resistor capable of generating heat which is then conducted to the skin. The enclosure M5 may hold the entire device or the power source may be external to the container M5. If the device is designed to be handheld the enclosure M5 should be of a size that is easily held by the palm of the hand of even a petit operator. Thus the lateral dimension M7 of the enclosure M5 should be between about 1 cm and about 7 cm and preferably between about 2 cm and 4 cm. The enclosure M5 should also be ergonomically shaped for easy use and handling by the user. The device can be designed as a hand held instrument. In this case the power source M10 may be inside the enclosure or it may external to it. If the energy source M10 is electrical energy source such as a power supply or power outlet or wall plug, electrical wire may be used to bring the energy into the enclosure M5. If the energy source is an compact electrical source such as a battery it may be placed inside the enclosure M5.

Figure 26:
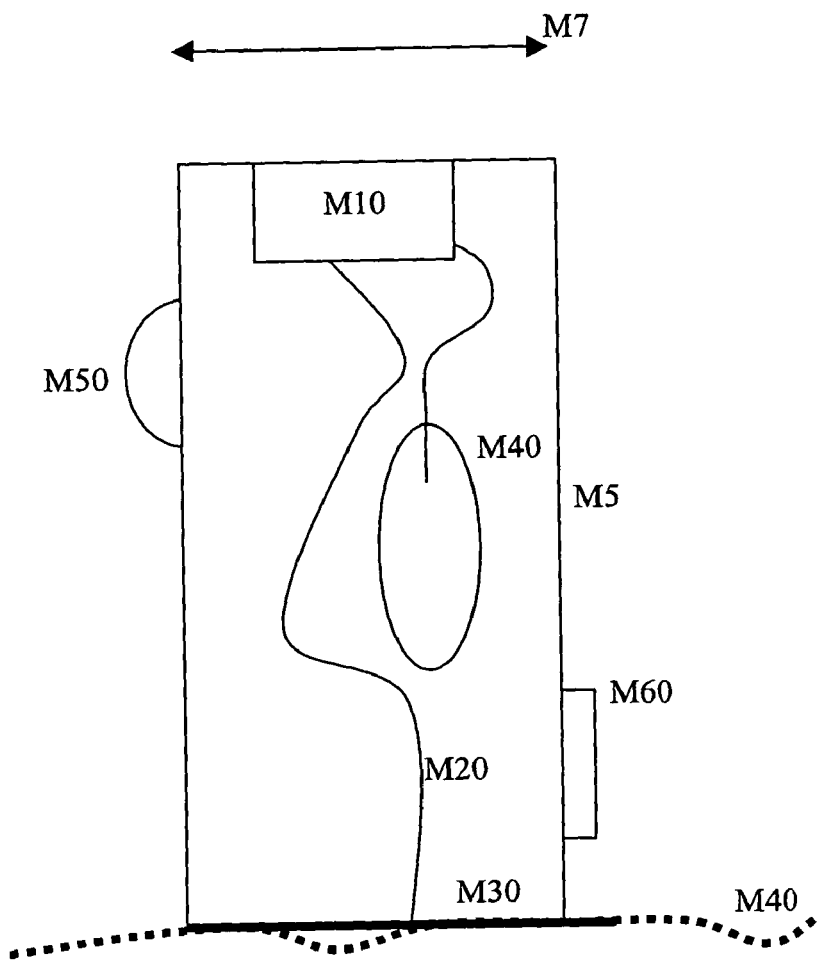
FIG. 26 is a sectional view showing possible components of an electrical and light thermal energy generator handheld acne treatment device.

FIG. 26 illustrates yet another preferred embodiment for treating skin conditions including acne. Here a control board M40 allows the user to willfully determine the duration and amount of energy delivered to the treating head. The duration of the energy delivery time is generally designed to be between about 0.001 millisecond and about 15 seconds and preferably between about 0.1 millisecond and about 0.5 second. The amount of energy supplied by the energy source should be sufficient to raise the surface temperature between about 39° C. and about 400° C. and preferably between about 50° C. and about 300° C. FIG. 26 also shows a power control button M 60 that can be switched between the off position and different power levels, for example, low, medium and high power level. FIG. 26 also shows a fire button M50 that allows triggering of the circuit board that in turn triggers the release of energy from the energy source to the treatment head.

Figure 27:
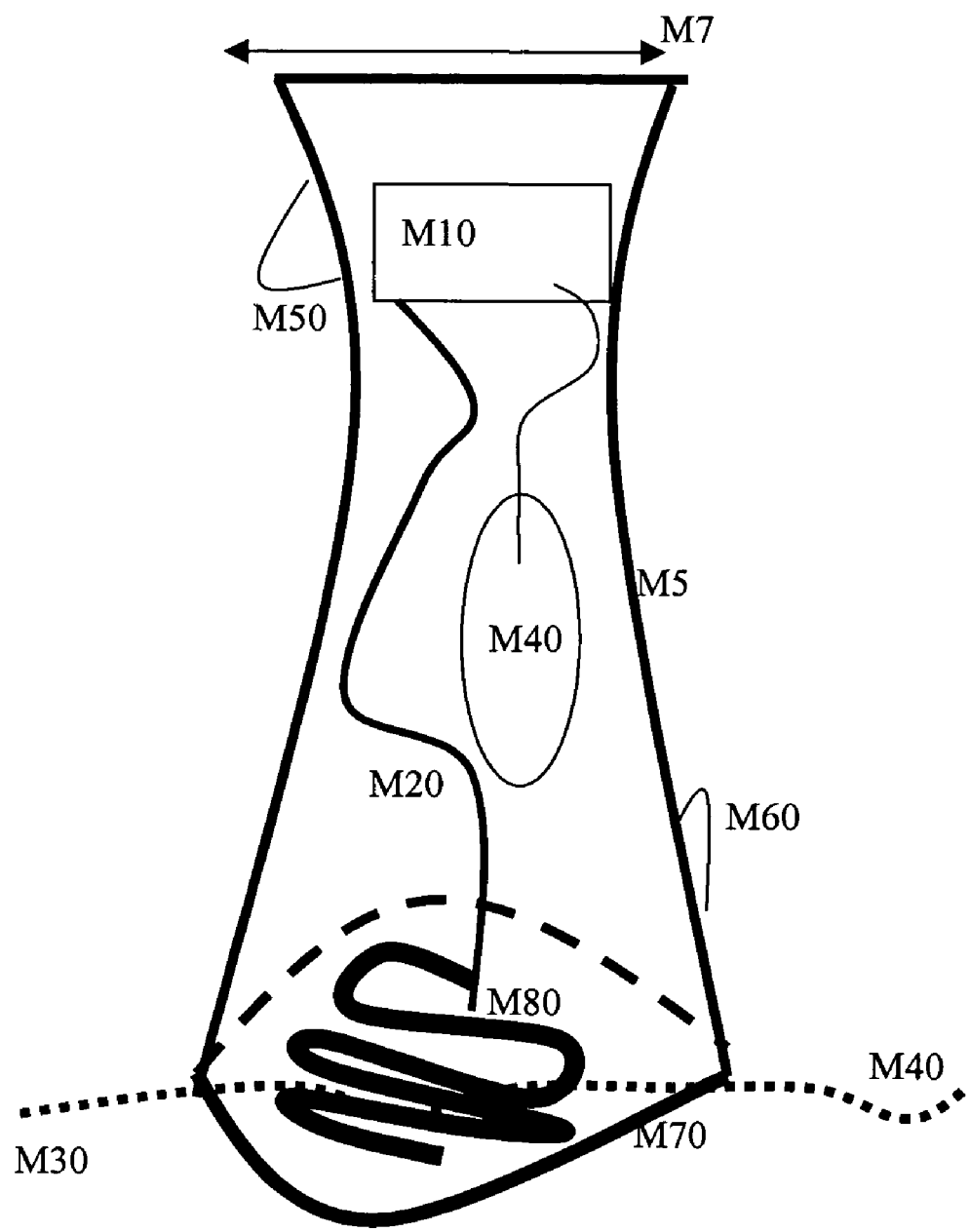
FIG. 27 is sectional view showing another possible component configuration of an electrical and light thermal energy generator handheld acne treatment device.

FIG. 27 shows a preferred embodiment wherein an electric source energy M10 delivered a pre-determined amount of energy through an electric current via a wire M20 to a resistive heating element M80 or a thermoelectric cooler M80 designed to heat and or cool (by switching polarity), placed at a footplate M70 which is in contact with the target tissue and preferably skin surface. Preferably the amount of energy delivered to the skin is sufficient to cause skin expansion so that skin pores expand and allow enhanced material transport across the surface, or sterilize bacteria or unwanted organisms within the tissue, or both.

Such electrical energy source should supply energy that should be sufficient to raise the surface temperature to between about 39° C. and about 400° C. and preferably between about 50° C. and about 300° C. for time duration between about microsecond and 100 seconds and preferably between 1 millisecond and 2 seconds.

Figure 28:
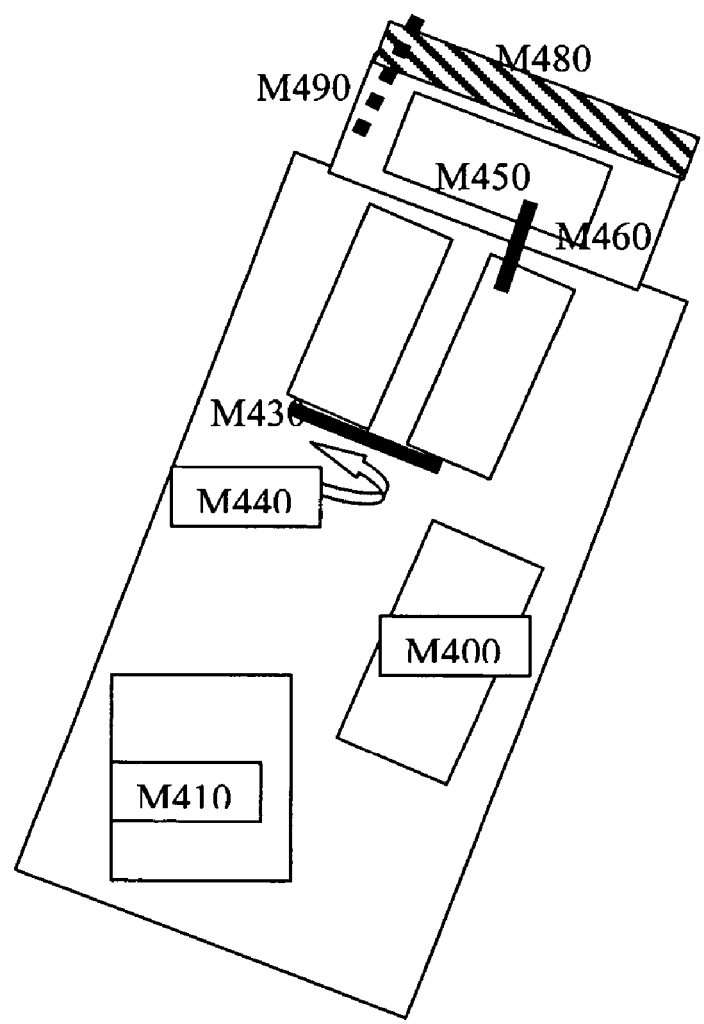
FIG. 28 is a sectional view showing possible components of a light or flash-lamp, or electromagnetic energy source handheld acne treatment device with a removable element of high absorbing substance.

FIG. 28 shows yet another preferred embodiment of the present invention designed to minimize charge time of the plurality of lamps. Here a plurality of batteries M410 charge a polarity of capacitors M420, mounted on a rotating plate M430. When the capacitors are rotated in the direction of the arrow M440, a different capacitor is brought into electronic connection with the flash lamp M450 via the electrical contact M460. The electronic board M400 controls the process of charging and rotating the plate M430. An optional absorbing plate M480 can be brought in as an intermediate media that converts the light energy into heat and brought into contact with the skin surface. This can be accomplished, for example, by swinging the absorbing plate on an axis M490 in and out of the lamp light pass.

Figure 29:
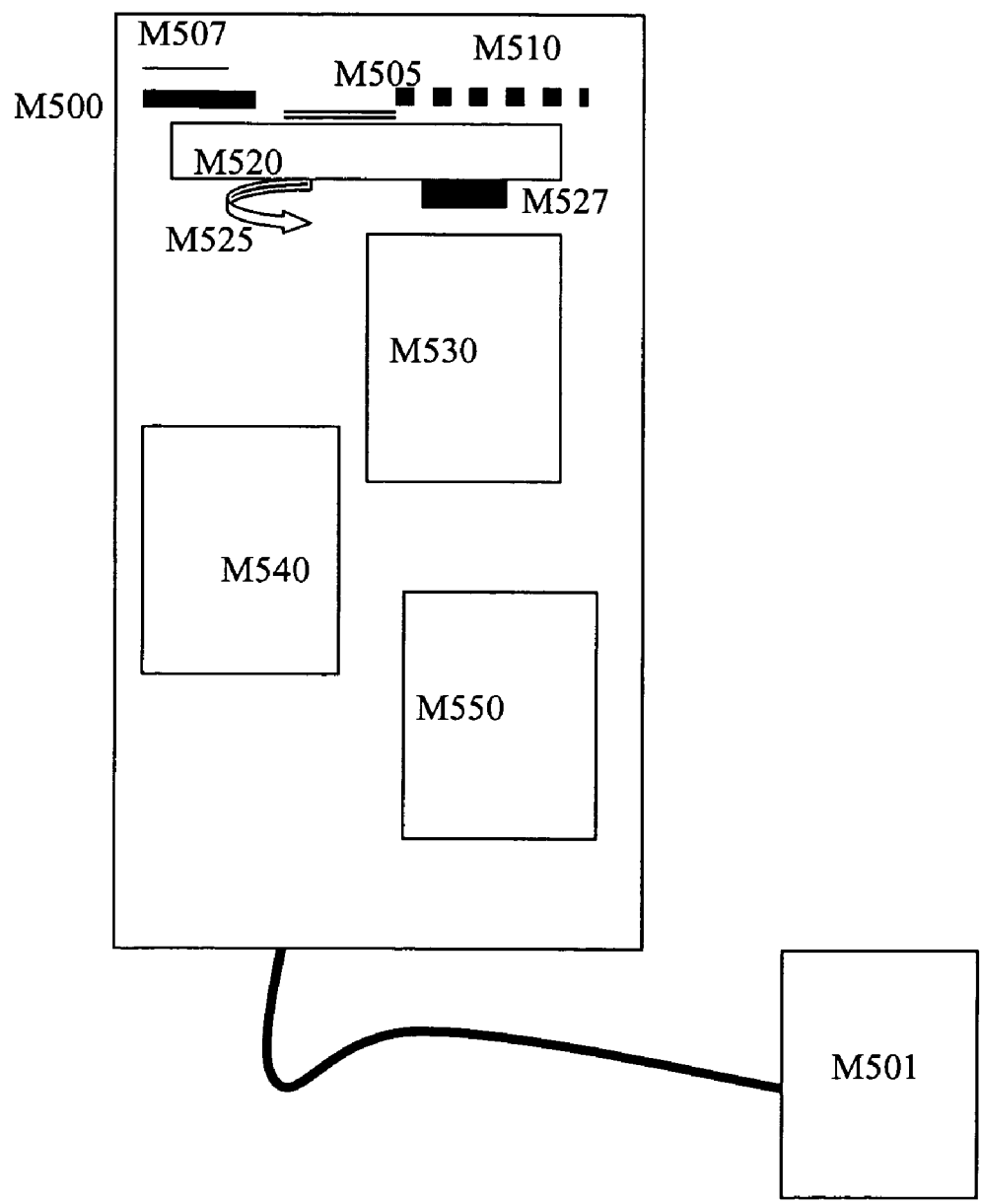
FIG. 29 is a sectional view showing possible components of an optical light, flash lamps, electric heater, or mechanical treatment switchable treatment windows.

In yet another preferred embodiment, FIG. 29 shows the device contemplated by the present invention wherein, on a rotating or stationary plate M520, a plurality of treatment heads are positioned. The treatment head can be made of a flash lamp, for example a xenon flash lamp M500 with an optional absorbing or partially absorbing interacting layer M507 placed in front of said window. An electrical heater window M505 with an electric resistor for heating or cooling the surface. In this case, an exemplary thermoelectric cooler can be used for example to heat or cool the target surface to a desired temperature in order to open pores or sterilize. Additional, rapid electric heater M510 can be used with an electric pulse sufficient to heat the surface of the target skin to a desired temperature, for a desired length of time. (For example, heating to a temperature range between 40° C. and 350° C. and preferably between about 200° C. and about 330° C., for duration of from about 0.1 ms to about 10 seconds and preferably between 1 ms and 250 ms). Yet another preferred embodiment contemplates additional treating head made of abrasive material, carrying chemical solutions, or delivering vacuum suction or a stream of abrasive particles.

These plurality of treatment heads can be, for example, mounted circularly on the rotating plate M520 and be rotated to deliver a treatment to the targeted surface in sequence or simultaneously. The rotation of the plate is indicated by the arrow M525. Such, heating, (by electrical or optical means) abrasive action, applications of chemicals, and vacuum suction are directed towards opening skin pores and opening, mitigating undesirable skin conditions and skin diseases, enhancing trans-dermal transport, and also reducing longer term skin pore sizes and enhancing the appearance of the skin. Again, the lamps, resistors, or thermo-electric coolers may be powered by capacitors M530 and an energy source M550 or an external energy source M501, and are controlled by an electronic control board M540. The electric heater, Thermo-electric cooler, rotating motor M527 and vacuum sources may be powered by a non-pulsing electric energy source M550 or M501.

Thee following embodiments are a method for treating a target surface:

The method comprises the steps of a) activating a an energy source, b) bringing an energy transporter element into contact with said heat source, c) allowing said energy transporter element to absorb some of the energy from the heat source, d) disconnecting said energy transporter and moving it into contact with target surface, e) allowing a predetermined amount energy from said energy transporter to be transferred to a target surface so that a desired effect is achieved, wherein the desired effect is a physical, chemical or biological effect, or a thermal change in the target surface characteristics, or a thermal expansion of the target surface, or a thermal expansion of the skin allowing opening of the skin pores so that said expansion allows at least some enhancement of material transport through said skin pores.

A device for thermal material conditioning comprises:

a. a heat source elevated to the desired temperature and maintained at said desired temperature.

b. a heat shuttle in contact with the heat source so that thermal energy can diffuse from the heat source and maintain said heat shuttle at the same temperature as the heat source.

c. a trigger that allow an operator to willfully released from contact with the heat source and is delivered and brought into contact with the taret treatment area so that thermal energy can flow from the heat shuttle to the targeted treatment material.

d. allowing said heat shuttle to maintain contact with the targeted treatment area of the target material for a period of time sufficient to bring the target material and the heat shuttle into thermal equilibrium so that substantially no heat flow from the heat shuttle to the targeted material.

e. aemoving the heat shuttle from contact with the target surface and bringing it back into a contact with the heat source.

In the method the heat shuttle is allowed to maintain contact with the targeted material area for a period of time from about 0.1 microsecond to about 1 second. The method further comprises bringing the target material surface to a temperature of between about 45 degrees Celsius and 500 degrees Celsius. The method further comprises using the human skin as a target material. The method further comprises bringing the target material surface to a temperature that results in expansion of the skin surface. The method further comprises bringing the target material surface to a temperature that results in effective increase of pore size by at least about 1 micrometer in diameter. The method further comprises repeating all steps at a repetition rate of between about 0.1 Hz and about 1 KHz, and preferably between 0.2 Hz and 10 Hz. In the method the heat source is electrical source of energy In the method the heat source is a thermoelectric cooler. In the method the heat shuttle is made of metal, such as a thin metal sheet of between about 1 micrometer in thickness and about 10 mm in thickness and preferably between about 70 micrometer and 200 micrometer. The target material is skin.

A device for skin conditioning comprises:
a heat source
a heat shuttle in contact with said heat source
a console to contain both the heat source and the Heat shuttle
a transfer compartment capable of separating the heat shuttle from the heat source, and transferring it into contact with the target material, keeping the heat shuttle in contact with said target material for a predetermined period of time, and then removing the heat shuttle from the target material and transferring it back into contact with the heat source.

A device is capable of repeatedly and automatically heating a target material by
bringing a Heat Shuttle into high temperature through by keeping the heat shuttle in contact with a heat source,
moving the heat shuttle away from the heat source and into contact with a target material to be heated,
maintaining contact between the heat shuttle and the target material for a predetermined length of time,
removing the heat shuttle from the target material and brining it back into contact with the heat source and repeating said steps for a predetermined period of time or a predetermined number of repetitions.

In the present invention the heat shuttle is kept in contact with the skin target material for a sufficiently long time to allow expansion of the skin so that at least one skin pore expands and opens enough to allow enhanced material transport through said at least one skin pore.

A aevice for treating material conditions comprises:
a heat source,
a heat shuttle in contact with said heat source
said heat shuttle comprises a body capable of loading up evenly with thermal energy and two latches.

One latch is connected to a spring which tend to propels the heat shuttle towards the target material and keeps it in contact with said target material.

The second heat latch is picked up (hooked to) by a rotating motor which propels the heat shuttle back up and brings it back into contact with the heat source.

The latch is constructed with a slop so that the rotating motor eventually slips off it allowing the now compressed spring in constant contact with latch number one to propel the heat shuttle again into the target material.

The process is repeated until the operator stops.

In this embodiment the role of the spring and the motor is reversed, i.e. the motor is the one pushing the heat shuttle into the target material and the spring tends to drive the heat shuttle away from the target material and into contact with the heat shuttle.

A device for material conditioning comprises:
a magazine full of spring loaded individual heat shuttles (much as in a automatic machine gun magazine),
said heat shuttle bullets comprise of at least thin aluminum floor to be loaded with heat energy and two latches,
a spring pushing against one latch in order to allow it to create a good thermal contact with the heat source,
a motor driving against the other latch to push the heat shuttle down away from the heat source and into contact with the target material,
a remover arm pushing the spent heat shuttles (whose thermal energy was used) away from the device and disposing of them),
a loader arm pushing the "bullets" heat shuttles into place where they can be picked up by the spring loading mechanism and be pushed into contact with the heat source.

A motor is used to drive a piston up against a spring (spring loading mechanism). The spring discharge after a stop at the station that allows it to load up with thermal energy. The shuttle is thus propelled by the spring towards the target material to be treated.

The amount of heat energy that was loaded up into the shuttle is finite, so the amount of heat or thermal energy that is discharged into the target material is finite as well.

Acne Contact device for Home use and Thermal Skin Conditioning for Home use
Additional Embodiment are as follows:
A method for Material Conditioning comprising:
a) A heat source brought to a desired temperature and maintained at that temperature
b) A Heat Shuttle (HS) maintained at the source temperature through thermal contact with the Heat Source.
c) Means to willfully trigger said heat shuttle (HS) motion so it is released from thermal contact with said heat source and is brought into thermal contact with the targeted treatment area
d) Allowing said heat shuttle to maintain contact with the treatment area for a period of time sufficiently long to transfer sufficient thermal energy to the targeted region to cause thermal expansion of the treated area and bring about the desired effects including the treatment of skin conditions
e) Removing the HS from contact with the targeted area and bringing it back into thermal contact with the heat source In the method the period of contact between the heat shuttle and the treatment area is from about 0.1 ms to about 1 second and preferably from about 1 ms to about 100 ms (In water-like material such a period of 100 ms will allow thermal energy to diffuse to roughly a depth of penetration of about 300 um).

The method further comprises repeating all steps at the repetition rate of between 0.1 Hz and 1 KHz and preferably at a repletion rate of between 0.2 Hz and 10 Hz.

In the method the heat source is powered by electrical heater driven by electrical energy.

In the method the heat source is a thermo-electric cooling device (TEC) or Paltrier cooling device.

In the method the heat shuttle is made of metal of sufficient contact area with the target material to allow reasonable work rate and preferably a contact area with the target material of between about 0.2 cm$^2$ and 4 cm$^2$.

In the method the heat shuttle is made of metal of sufficient volume and heat capacity to allow the heat shuttle to carry thermal energy sufficient to raise the temperature of the upper layers of the skin to cause the desired effect and in particular to improve or cure undesired skin conditions.

In the method the Heat Shuttle (HS) is made of thermally conducting material in the form of a sheet with a thickness of between about one micrometer and about one millimeter in thickness and preferably between 70 micrometer and 200 micrometer.

A device for material conditioning comprises:
a heat source,
a heat shuttle in contact with said heat source,
a console to contain both the heat source and the heat shuttle (HS) and to ensure that neither is in thermal contact with the target treatment area during at least part of the device operation time,
a transfer element capable of separating the heat shuttle from the heat source and brining it into contact with the target material keeping the heat shuttle, keeping the heat shuttle in contact with said target material for a predetermined period of time then removing the HS from the targeted material and bringing the HS back into thermal contact with the heat source.

The device further comprises keeping the HS in contact with the target material for a sufficiently long time to allow thermal expansion of the target material.

The device further comprises a pump to lower the pressure within the device chamber and create a tighter seal to the skin. This will allow: better contact with the skin, removal of debris from the skin and pores, and reduction of the amount of air within the chamber in order to minimize heat conduction and heat removal from the HS during it passage from the heat source to the targeted skin.

In the Devices of the present invention, the heat shuttle can be coated with drug or any other substance that is desirable to deliver into the target surface. A drug or any other substance can be applied to the same area of the skin before, during, or after the action of the heat shuttle.

In the device, a container and dispenser containing and dispensing a drug or any other substance that one wishes to deliver into the target surface is attached to the heat shuttle apparatus and delivers a desirable substance before, during or after the action and passage of the heat shuttle.

A therapeutic treatment device comprises:

an incoherent electromagnetic energy source operable to provide a pulsed energy output from a plurality of energy sources having a spectrum of frequencies including a frequency bandwidth capable of being absorbed by an intermediate substance;

a housing with an opening, said light source being disposed in said housing, and said housing being suitable for being disposed adjacent to the intermediate substance;

a variable pulse-width pulse forming circuit electrically connected to said light source; a reflector mounted within said housing and proximate said light source, directing its energy towards said absorbing intermediate substance whose absorbing characteristics range from zero (completely transmitting) to infinity (completely absorbing), wherein the fluence is less than 2 J/cm$^2$, preferably less than 1 J/cm2. The incoherent energy source is supplemented with a laser energy directed at the general vicinity of the treatment area before, during or after the application of the pulsed energy output. Substantially most of the energy of the electromagnetic source is deposited at the surface resulting in expansion of skin surface opening and discontinuities to allow at least some enhancement in the transport of material across the skin to alleviate skin conditions and ailment and to improve the look and condition of the skin.

The plurality of energy sources can be lamps with reflectors with electromagnetic energy output and at least one lamp energy is intercepted by a high absorbing film mounted proximate to the lamp opening. Said energy source can be a light source, or a flash lamp such as of the type used in digital and disposable (single use) cameras. Said energy source comprises means for providing pulses having a width in the range of between about 0.5 microseconds and 500 millisecond and an energy density of the light on the skin of more than about 0.1 J/cm$^2$. and less than about 2 J/cm2.

Said energy source comprises means for providing a pulse in the range of about 0.1 milliseconds to 2000 milliseconds, whereby skin opening may be expended to enhance transport across the skin.

Said energy source comprises means for providing pulsed electromagnetic energy in the range of about 0.1 millisecond and about 1000 milliseconds, and providing laser CW light radiation before, during, or after said pulse radiation. Said energy source comprises means for providing pulsed electromagnetic energy in the range of about 0.1 millisecond and about 1000 milliseconds, and providing laser CW light radiation before, during, or after said pulse radiation and providing lamp radiation before, during, after, and is able to heat the dermis/epidermis junction temperature to between about 45 degree C. and 55 degree C. Said energy source comprises means for providing pulsed electromagnetic energy in the range of about 0.1 millisecond and about 1000 milliseconds, and providing lamp radiation before, during, after, and is able to heat the dermis/epidermis junction temperature to between about 45 degree C. and 55 degree C.

Said energy source comprises means for providing pulsed electromagnetic energy in the range of about 0.1 millisecond and about 1000 milliseconds, and providing lamp radiation before, during, after, and is able to heat the dermis/epidermis junction temperature so that combined with the energy deposited in the skin by pulse EM energy source, skin conditions are alleviated including the condition of acne.

Said light source comprises means for providing pulses having a width in the range of between substantially 0.05 microsecond and 1000 millisecond and an energy density of the light on the skin of less than about 10 J/cm$^2$.

Said light source comprises means for providing pulses having a width in the range of between substantially 0.1 millisec and 600 millisec and an energy density of the light on the skin of less than about 6 J/cm$^2$.

Said light source comprises means for providing plurality of pulses having a width in the range of between substantially 0.1 millisec and 600 millisec and an energy density of the light on the skin of more than 2.5 J/cm$^2$.

circuit.

I claim:

1. A device for treating skin by delivering a controlled amount of thermal energy to the skin comprising:
   a hand-held enclosure; and
   a heat-providing portion configured to deliver the controlled amount of thermal energy to the skin, the heat-providing portion comprising:
      a flash lamp for emitting optical energy;
      a reflector for directing the optical energy emitted from the flash lamp;
      a circuit having a capacitor, the circuit configured to deliver a predetermined amount of energy via the capacitor to the flash lamp; and
      an absorbing layer being placed between the flash lamp and the skin and capable of absorbing the optical energy discharged by the flash lamp and converting it into thermal energy;
      a heat delivery surface positioned on an external portion of the device and configured to be placed against the surface of the skin, the heat delivery surface configured to transmit the thermal energy to the skin, the heat delivery surface having an area of 0.2 cm$^2$ to 4 cm$^2$;
   wherein the controlled amount of thermal energy provided to the skin is between 0.1 J/cm$^2$ and 50 J/cm$^2$, and the controlled amount of thermal energy is provided in a delivery time of less than 0.5 second.

2. The device of claim 1, wherein the absorbing layer comprises a pattern of absorbing and transmitting regions.

3. The device of claim 1, wherein the absorbing layer is supported on a transparent substrate.

4. The device of claim 1, wherein the absorbing layer is made of absorbing metal.

5. The device of claim 1, wherein the absorbing layer is made of absorbing insulator.

6. The device of claim 1, further comprising a power source electrically coupled to the capacitor of the circuit, wherein the capacitor is charged by the power source and discharged by a user-operated external trigger.

7. A method for treating skin conditions comprising:
   providing a device comprising a circuit having a capacitor, wherein the circuit is configured for charging a capacitor from a power source and for releasing a pre-determined amount of energy from the capacitor, wherein the circuit comprises a power button configured to activate charging of the capacitor from the power source, and the circuit further comprises a discharge button configured to activate release of the pre-determined amount of energy from the capacitor;

providing a heating element configured to absorb at least some of the energy discharged from the capacitor and converting it to thermal energy, wherein the heating element comprises a heat transfer surface and a flash lamp configured to convert the energy discharged from the capacitor into optical energy, the heating element further comprising an absorbing substance configured to absorb optical energy from the flash lamp and convert it into thermal energy, and wherein the heat transfer surface has an area of 0.2 $cm^2$ to 4 $cm^2$;

switching the power button to activate charging of the capacitor by the power source;

bringing the heat transfer surface adjacent to and against the skin to be treated; and switching the discharge button to activate release of the pre-determined amount of energy from the capacitor to the heating element to thereby heat an upper layer of the skin to a temperature in the range from 50° C. to about 400° C., wherein the amount of thermal energy provided to the skin is between 0.1 $J/cm^2$ and 50 $J/cm^2$.

8. The method of claim 7 wherein the layer below the epidermal dermal junction remains below 50° C.

9. The method of claim 7 wherein the layer below the mid-reticular dermis remain below about 50° C.

10. The method of claim 7 wherein the layer below the dermal epidermal junction remains below about 50° C. and at least some changes in the opening at the skin surface occurs.

11. The method of claim 7, wherein bringing the heat transfer surface adjacent to and against the skin comprises placing the absorbing substance adjacent the skin, the method further comprising:

disengaging the absorbing substance from the skin; and
emitting optical energy directing onto the skin.

* * * * *